(12) United States Patent
Powell et al.

(10) Patent No.: US 6,548,287 B1
(45) Date of Patent: *Apr. 15, 2003

(54) NON-PYROGENIC BACTERIAL STRAINS AND USE OF THE SAME

(75) Inventors: Robert J. Powell, Baltimore, MD (US); David M. Hone, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/339,180

(22) Filed: Jun. 24, 1999

Related U.S. Application Data

(62) Division of application No. 08/802,371, filed on Feb. 19, 1997, now Pat. No. 5,997,881.
(60) Provisional application No. 60/007,478, filed on Nov. 22, 1995.

(51) Int. Cl.[7] .................. A61K 39/10; A61K 39/108; A61K 39/05; A61K 39/112; A61K 39/106
(52) U.S. Cl. ............. 435/243; 424/234.1; 424/241.1; 424/245.1; 424/253.1; 424/258.1; 424/260.1; 424/261.1; 424/7; 424/240; 424/249.1; 435/69.3; 435/170; 435/252.3
(58) Field of Search ................ 424/234.1, 241.1, 424/245.1, 253.1, 258.1, 260.1, 261.1, 240.1, 249.1; 435/69.3, 170, 172.1, 243, 252.3

(56) References Cited

U.S. PATENT DOCUMENTS

| | | | | |
|---|---|---|---|---|
| 4,595,660 A | | 6/1986 | Ostroff et al. | 435/172.3 |
| 5,561,064 A | | 10/1996 | Marquet et al. | 435/320.1 |
| 5,997,881 A | * | 12/1999 | Powell et al. | 424/234.1 |
| 6,080,849 A | * | 6/2000 | Bermudes et al. | 536/23.7 |

FOREIGN PATENT DOCUMENTS

WO  WO95/21250  8/1995

OTHER PUBLICATIONS

Camilli, et al. Insertional mutagenesis of listeria monocytogenes with a novel Tn917 derivative that allows direct cloning of DNA flanking transposon insertions. Jour. Of Bact., Jul. 1990 p. 3738–3744.

Golenbock, et al. Lipid A–like molecules that antagonize the effects of endotoxins on human monocytes. Jour. Of Bio Chem. 266:29, 1991, 19490–19498.

Lee, et al. Mutation of the htrB locus of Haemophilus influenzae nontypable strain 2019 is associated with modifications of lipid A and phosphorylation of the lip–oligosaccharide. Jour. Of Bio Chem. 270:45, 1995, p. 27,151–27159.

Hansson, M., et al., "Single–Step Recovery of a Secreted Recombinant Protein by Expanded Bed Adsorption", *Bio/Technology*, Mar. 1994; 12:285–288.

Karow, M. et al., "Isolation and Characterization of the *Escherichia coli htrB* Gene, Whose Product Is Essential for Bacterial Viability above 33°C in Rich Media", *J. of Bacteriology*, Jan. 1991; 173(2):741–750.

Karow, M. et al., "Isolation and Characterization of the *Escherichia coli MSb* Gene, a Multicopy Suppressor of Null Mutations in the High–Temperature Requirement Gene htrB", *J. of Bacteriology*, Feb. 1992; 174(3):702–710.

Schorr et al., "Large Scale Purification of Endotoxin–Free Plasmid DNA for Gene Therapy Research", In: Gene Therapy Meeting Cold Spring Harbor (149). New York: 1994; pp. 21–25 ( 1 page abstract only).

Servos et al. 1996. Gene. 175: 137–141.*

Somerville et al. 1996. J. Clin. investigations. 97(2):359–365.*

Karow et al 1992. J. of Bacteriology. 174(3): 702–710.*

Karow et al. 1991. J. of Bacteriology. 173(2): 741–750.*

* cited by examiner

*Primary Examiner*—Lynette R. F. Smith
*Assistant Examiner*—JaNa Hines
(74) *Attorney, Agent, or Firm*—Steven J. Hultquist

(57) ABSTRACT

The present invention provides gram-negative bacterial strains that produce substantially pure non-pyrogenic lipopolysaccharide or lipid A. The present invention also relates to a use of said strains for the preparation of non-pyrogenic DNA and use of the same for introducing endogenous or foreign genes into animal cells or animal tissue. Further, the present invention relates to a use of said strains for the preparation of non-pyrogenic recombinant mammalian, protozoan and viral proteins. Furthermore, the present invention relates to a use of said strains for the preparation of non-pyrogenic bacterial vaccines and vaccine vectors. Yet a further use of the present invention relates to a use of said strains for the preparation of non-pyrogenic bacterial proteins and polysaccharides antigens for use as vaccines.

9 Claims, No Drawings

NON-PYROGENIC BACTERIAL STRAINS AND USE OF THE SAME

CROSS REFERENCE TO RELATED APPLICATION

This application is a division of Ser. No. 08/802,371 filed Feb. 19, 1997, now U.S. Pat. No. 5,997,881.

Priority of this application is based on provisional application Ser. No. 60/007,478, filed Nov. 22, 1995.

FIELD OF THE INVENTION

The present invention provides gram-negative bacterial strains that stably produce substantially-pure non-pyrogenic lipopolysaccharide or lipid A. The present invention also relates to the use of said strains for the preparation of non-pyrogenic DNA and use of the same for introducing endogenous or foreign genes into animal cells or animal tissue. Further, the present invention relates to a use of said strains for the preparation of non-pyrogenic recombinant mammalian, protozoan and viral proteins. Yet a further use of tile present invention relates to a use of said strains for the preparation of non-pyrogenic bacterial proteins and polysaccharides antigens for use as vaccines. Furthermore, the present invention relates to a use of said strains for the preparation of non-pyrogenic live and inactive bacterial vaccines and vaccine vectors.

BACKGROUND OF THE INVENTION

1. The Use of Bacterial Host Strains in Biotechnology

Medical biotechnology now encompasses a broad range of medical technologies that have veterinary and human applications. At the crux of this technology is the use of recombinant DNA, molecular biochemistry and immunochemical techniques, which allow the identification, characterization and manufacture of proteins and polysaccharides. One of the first products produced using these techniques was cloned recombinant human insulina. Since it's initial implementation, biotechnology has enabled the development of a large array of biological products that have therapeutic or vaccinal properties (Crommelin and Schellekens (eds), in: *From clone to clinic*, Kluwer Academic Publishers, Dorddrecht, The Netherlands (1990); The Biotol Team (eds), In: *Biotechnology innovations in health care*. Butterworth-Heinemann Ltd, (1991); Reidenberg (ed), In: *The clinical pharmacology of hiotechnology products*, Elsevier Science Publishers (1991)).

One of the biotechnology "work horses" are the bacterial host strains, which are used to house cloned genes and for the large scale production of the cloned genes or the products of said cloned genes. Examples of these bacterial hosts strains include HB101, DH5, DH5α, DH5αMCR, DH10, DH10B, C600 or LE392 (Grant et al, Proc Natl Acad Sci (USA) 87:4645–4649 (1990); Sambrook et al (eds), In: *Molecular Cloning*, Cold Spring Harbor Press, Cold Spring Harbor, N.Y. (1993)). These host strains are designed to stably harbor and express clones genes.

A major problem, however, associated with using bacterial host strains is the process of removing bacterial LPS from the final products. The biological properties of LPS have been extensively investigated (Rietschel et al, *FASEB*, 8(2): 217–225 (1994); Raetz, *J Bacteriol*, 175(18):5745–5753 (1993); and Alving, *Immunobiol*, 187:430–446 (1993)). This molecule has powerful pyrogenic activity, so that in humans nanogram quantities of LPS can induce febrile responses, which are mediated by host proinflammatory cytokines IL-1, IL-6, and TNF-α (Mackowiak (ed), In: *Fever: Basic mechanisms and management*. Raven Press, NY (1991); Abernathy and Spink, *J Clin Invest*, 37:219–226 (1958); Greisman et al, *J Clin Invest*, 43:1747–1757 (1964); Rietschel et al, supra; and Raetz, supra (1993)). For this reason, the United States Food and Drug Administration have strict guidelines on the level of LPS that is acceptable in biomedical products (*Good Manufacturing Practices*, In: *US Code of Federal Regulation* 210–211; and *Protection of human subjects*, US Code of Federal Regulation 50, Food and Drug Administration, CBER, Rockville Md.). Since all the currently available host strains produce pyrogenic LPS, this activity must be removed to acceptable levels, resulting in additional manufacturing costs.

2. Gene Therapy and Genetic Immunization

The commercial applications of DNA delivery technology to animal cells are extremely broad and includes delivery of vaccine antigens (Fynan et al, *Proc. Natl. Acad. Sci., USA*, 90:11478–11482 (1993); Katsumi et al, *Hum Gene Ther*, 5(111:1335–1339 (1994); Spooner et al, *Int J Oncol*, 6(6):1203–1208 (1995)), immunotherapeutic agents (Shillitoe et al, *Eur J Cancer* 30B(3):143–154 (1994); Hengge et al, *Nature Genetics*, 10(2):161–166 (1995); Vile and Hart, *Ann Oncol*, 5(Suppl 4):59–65 (1994); Miller et al, *Ann Surg Oncol*, 1(5):436–450 (1994); Foa, *Baillieres Clin Haematol*, 7(2):421–434 (1994)), and gene therapeutic agents (Darris et al, *Cancer*, 74(Suppl 3):1021–1025 (1994); Magrath, *Ann. Oncol.*, 5(Suppl 1):67–70 (1994); Milligan et al, *Ann. NY Acad. Sci.*, 716:228–241 (1994); Schreier, *Pharma. Acta Helv.*, 68:145–159 (1994); Cech, *Biochem. Soc. Trans.*, 21:229–234 (1993); Cech, Gene, 135:33–36 (1993); Dropulic and Jeang, *Hum Gene Ther*, U5(8):927–939 (1994); Sorscher et al, *Hum Gene Ther*, 5(10):1259–1277 (1994); Woo, *Trends Genet*, 10(4):111–112; Long et al, *FASEB J.*, 7:25–30 (1993); Nabel et al, *Hum Gene Ther* 5 (9):089–109 (1994); Manthorpe et al, *Hum Gene Ther*, 4(4):419–431 (1993); Mittal et al, *Virus Res*, 28:67–90 (1993); Setoguchi et al, *Am J Respir Cell Mol Biol* 10:369–377 (1994); and Rosi et al, *Pharm. Therap.*, 50:245–254 (1991)).

In the aforementioned applications prolonged expression of the eukaryotic expression cassette once in the host tissue is highly desirable (Yang et al, *J Virol*, 69(4):2004–2015 (1995); Wicks et al, *Hum Gene Ther*, 6(3):317–323 (1995) and Alton et al, *Nature Genet*, 5(2):135–42 (1993)). Unfortunately, adenoviral vectors have proven to he highly immunogenic and induce a host responses against cells containing these vector (Yang et al, supra). This host response causes a more rapid clearance of the cells carrying adenovirus-delivered eukaryotic expression cassettes. Similarly, induction of inflammation at the site of "naked" DNA introduction or treatment with DNA encapsulated in cationic lipids can be deleterious to the elicitation of prolonged expression of the introduced eukaryotic expression cassette (Wicks et al, supra). A major cause of inflammation after introduction of DNA into the host is LPS, which co-purifies with DNA (Wicks et al, supra). LPS is a notorious biologically active molecule with potent pyrogenic properties (Mackowiak (ed), supra); Rietschel et al, supra; Raetz, surpa (1993); and Alving, *Immunobiol*, 187:430–446 (1993)).

Thus, sophisticated DNA purification procedures have been devised that remove LPS from the DNA prior to introduction into the host (Yang et al, supra; Nabel et al, supra; and Manthorpe et al, supra). These purification procedures involve removal of LPS with ionic detergents such as Triton X-114 or using polymyxin B columns (Yang et al, supra; Nabel et al, supra; and Manthorpe et al, supra). A weakness of this approach is that it adds additional cost to the commercial production of DNA and even after such purification procedures significant quantities of LPS remains associated with the DNA (Yang et al, supra; Nabel et al, supra; and Manthorpe et al, supra). This LPS will enter the host cells that receive the DNA encoding the eukaryotic expression cassette and exert it's biological effects. Higher primates are more sensitive to LPS than laboratory rodents and under certain pathological conditions states of LPS hypersensitivity can be induced (Mackowiak (ed), supra); Abernathy and Spink, supra; and Greisman et al, surpa). Therefore, it is paticularly important to produce DNA preparations that are free of LPS pyrogenic activity for applications in humans.

3. Bacterial Strains in Vaccine Development

Inactivated and live attenuated bacteria are effective as vaccines (Holmgren et al, In: *Vibrio cholerae and cholera*. Wachsmuth et al. (eds), ASM Press Washington D.C., pp 415–424 (1994); Woodrow and Levine (eds), In: *New Generation Vaccines*, Marcel Dekker, New York (1990); and Cryz (ed) in: *Vaccines and immunotherapy*, Pergamon Press New York (1991)) and as vector vaccines for the delivery of passenger antigens from other pathogens to the host immune system (Woodrow and Levine (eds), supra; and Cryz (ed) supra). In the role of vaccine vector, bacterial vaccines have the capacity to deliver bacterial antigens from bacterial pathogens, protozoan antigens, and viral antigens (Woodrow and Levine (eds), supra; and Cryz (ed) supra) ). In order to be a successful vaccine or vaccine vector the inactivated or live attenuated bacterial vaccines or vector vaccine must be genetically stable, well-tolerated by the recipient host and stimulate humoral and T cell-mediated immunity in the recipient.

At present there is an attenuated strain of *Salmonella typhi* that is licensed for use as a live oral typhoid vaccine, strain Ty21a. Ty21a was prepared by successive exposures of wild type strain Ty2 to the chemical mutagen N-methyl-N'-nitro-N-nitrosoguanidine. Consequent to this non-specific mutagenesis, Ty21a has mutliple mutations including those in galE and causing Ty21a to be Vi-negative. Ty21a is licensed in the USA where it is administered in a four dose immunization schedule.

Ty21a is an extremely well-tolerated live oral vaccine. Nevertheless, it suffers from many drawbacks that have been well-publicized in the scientific literature and it is well-recognized that a new and improved live oral typhoid vaccine is needed. The drawbacks of Ty21a include:

1) A Phase 1 volunteer study in which a defined *S. typhi* galE Vi-negative strain was ingsted showed that the combination of a mutation in galE and lack of a Vi capsule are insufficient by themselves to fully attenuate wild type strain Ty2, the parent from which Ty21a was derived.

Hence, the precise mutations that are responsible for the attenuation of Ty21a are not known and the task of defining the attenuating lesions in Ty21a might involve extensive genetic analysis as this strain was developed using non-specific chemical mutagenesis which introduces multiple point mutations in random locations on the target strain chromosome.

Since the introduction of recombinant DNA techniques into the field of vaccine development it is now possible to attenuated strains with specific and precise genetic mutations that cause defined affects to the virulence of the target organism. Thus to overcome this first shortfall of Ty21a future strains must be made by precise genetic techniques.

2) Ty21a has been disappointing in attempts to utilize it as a live vaccine vector. Two Ty21a-based constructs have been evaluated in clinical trials, a candidate vaccine against *Shigella sonnei* consisting of Ty21a harboring a *S. sonnei* plasmid that results in expression of *S. sonnei* O antigen (Formal et al, *Infect. Immun.*, 34:746–750 (1981)) and Ty21a having a plasmid allowing expression of the O antigen Vibrio cholerae O1 serotype Inaba (Forrest et al, *J. Infect. Dis.*, 159:145–146 (1989)). In each instance results of clinical trials were disappointing (Levine and Tacket, In: *Vibrio cholerae and cholera*. Wachsmuth et al. (eds), ASM Press Washington D.C., pp 395–413 (1994)) and further clinical trials were abandoned. With each of these hybrid vaccines the limitations of Ty21a as a live vector were pointed out.

Thus, there is clearly a need for an improved attenuated strain of *S. typhi* to serve as a live oral typhoid vaccine and as a live vector.

Some mutations are known to attenuate wild type Salmonella thereby rendering said mutants promising (well-tolerated and protective) as live vaccines in mice and calves. These include strains harboring deletions in cya and crp (cya and crp constitute a global regulatory system in Salmonella) or in one or more genes (aroA, aroC or aroD) that encode critical enzymes in the aromatic amino acid biosynthesis pathway (Woodrow and Levine, supra).

Three such candidates have been assessed in Phase 1 clinical trials, including $\chi$3927, a cya, crp mutant derived from wild type strain Ty2, CVD 908, a $\Delta$aroC, $\Delta$aroD mutant derived from Ty2 and CVD 906, a $\Delta$aroC, $\Delta$aroD mutant derived from wild type strain ISP 1820 (a minimally-passaged 1983 isolate from the blood culture of a Chilean child with uncomplicated typhoid fever) (Tacket et al, *Infect. Immun* 60:536–541 (1992); Tacket et al, *Vaccine* 10:443–446 (1992b); and Hone et al, *J. Clin. Invest* 90:412–420 (1992)).

These three live bacterial vaccine candidates were fed to adult volunteers in single doses of $5\times10^4$ or $5\times10^5$ cfu, with buffer, in a randomized, double-blind clinical trial (Tacket et al, supra (1992); Tacket et al, supra (1992b); and Hone et al, supra(1992)). Significant febrile responses were observed in some recipients of strains CVD 906 or $\chi$3927, so further clinical trials with these strains were abandoned (Tacket et al, supra (1992) and Hone et al, supra(1992)). In contrast, CVD 908 did not cause notable systemic reaction, so that additional dose response studies were carried out with CVD 908 (Tacket et al, supra (i992); Tacket et al, supra (1992b)).

In subsequent Phase 1 clinical trials with CVD 908 in which adult volunteers were orally vaccinated with freshly-harvested vaccine organisms, the vaccine was well-tolerated in single doses as high as $5\times10^7$ and $5\times10^8$ cfu (Levine, *Session* 57, American Society for Microbiology Annual Meeting, Washington D.C. (1995); and Levine, *Keystone meeting on mucosal immunity*, Keystone Colorado *J Cell Biochem* 19A:238 (1995)). However, when attention was turned to prepare definitive formulations of CVD 908 to be made from fermentor-grown organisms, certain limitations of the aro mutants became readily apparent. The quandry faced in preparing a definitive formulation is to be able to grow the vaccine organisms in sufficient p-aminobenzoic acid (PABA) to obtain high yields but to avoid retention of so much PABA in the lyophilate that the vaccine organism is capable of excessive growth in vivo (which might result in adverse reactions) (Levine, *Session* 57, American Society for Microbiology Annual Meeting, Washington D.C. (1995); and Levine, *Keystone meeting on mucosal immunity*, Keystone Colorado *J Cell Biochem* 19A:238 (1995). By carefully adjusting the concentrations of PABA and other aromatic metabolites in the growth medium and by utilizing other specific quality control steps in the production process, it is possible to prepare vaccine lots with the desired properties (Levine, *Session* 57, American Society for Microbiology Annual Meeting, Washington D.C. (1995); and Levine, *Keystone meeting on mucosal immunity*, Keystone Colorado *J Cell Biochem* 19A:238 (1995).

Nevertheless, an ideal attenuated strain for use as a live vaccine would not be subject to such stringent production constraints. Rather, an ideal attenuated strain would be one that could be manufactured in large scale with simpler production methods and less stringent growth medium requirements than those necessary for aro mutants.

Thus, in light of this practicallity issue with CVD 908 there is a need to develop new attenuated mutants of Salmonella that bear defined attenuating lesions, that are amenable to large-scale formulation and that retain the ability to stimulate high levels of T cell-mediated immunity as well as serum and mucosal antibody responses.

A similar phenomenon has been observed by investigators while developing live oral Vibrio cholerae strains. While live oral ΔctxA Vibrio cholerae strain CVD 103-HgR is well tolerated and immunogenic in volunteers (Levine and Tacket, supra), other ΔctxA mutants of *Vibrio cholerae*, which carry the identical mutation in the identical parent strain, have proven to be reactogenic (Levine and Tacket, supra). Thus, it is not clear what additional change causes CVD 103-HgR to be well-tolerated in volunteers. Further, *Shigella flexneri* 2a Δaro, ΔvirG mutant, CVD 1203 (Noriega et al, *Infect. Immun* 62: 5168–5172 (1994)) displayed impressive immunogenicity in volunteers but also caused mild diarrhea in a significant number of volunteers (Levine, *Session* 57, American Society for Microbiology Annual Meeting, Washington D.C. (1995); and Levine, *Keystone meeting on mucosal immunity*, Keystone Colorado *J Cell Biochem* 19A:238 (1995). This indicates that further attenuated derivatives of CVD 1203 must be developed before such mutants are acceptable for large scale clinical evaluation (Levine, *Session* 57, American Society for Microbiology Annual Meeting, Washington D.C. (1995); and Levine, *Keystone meeting on mucosal immunity*, Keystone Colorado *J Cell Biochem* 19A:238 (1995).

Bacterial host strains can also serve as vectors for the delivery of protective antigens cloned from other pathogens. As used herein the expression of "protective antigens" means antigens or epitopes thereof which give rise to protective immunity against infection by the pathogen from which they are derived.

The pathogens from which genes encoding protective antigens include protozoan (Sadoff et al, *Science*, 240:336–337 (1988)), viral (Wu et al, *Proc. Natl. Acad. Sci. USA*, 86:4726–4730 (1989)) and bacterial (Formal et al, supra; Clements et al, 46:564–569 (1984)) pathogens.

Additionally, *Escherichia coli* has been employed as a vaccine vector for the delivery Shigella antigens in volunteers (Formal et al, *Infect Immun* 46:465–470 (1984)). However, these recombinant strains have proven to be reactogenic. More recently, Vibrio strains have been used saucessfully as vaccine vectors in animal models (Butterton et al, *Infect Immun* 63:2689–2696 (1995)). It is likely, therefore, that any well-tolerated and immunogenic bacterial vaccine will have the potential to serve as a vaccine vector. While the bulk of the documented data discusses the use of live oral vaccine vectors, inactivated bacterial vaccine vector are also feasible (Cardenas et al, *Vaccine* 12:833–840 (1994)).

A key step toward the development of a multivalent bacterial vaccine vector, will be the development of attenuated, non-reverting, and immunogenic bacterial vaccines strains.

4. Bacterial LPS and Lipid A

Under normal conditions, LPS is inserted in the outer surface of the outer membrane of gram negative bacteria (Schnaitman and Klena, *Microbiol Rev*, 57:655–682 (1993); and Makela and Stocker, In: *Handbook of endotoxin volume* 1, Elsevier Biomedical Press, Amsterdam, Rietschel (ed), pp59–137 (1984)). Complete or "smooth" LPS is composed of three main domains called lipid A, the O-antigen (also called the O-polysaccharide) and the core region, which creates an oligosaccharide link between lipid A and the O antigen (Schnaitman and Klena, supra; and Makela and Stocker, supra). The O-antigen is composed of oligosaccharide repeat units. The structure and number of these repeats varies depending on the bacterial species and growth conditions, typically ranging from one to fifty repeats (Schnaitman and Klena, supra; and Makela and Stocker, supra). Some bacterial generi, such as Neiseria spp., produce LPS that has low numbers of O-antigen repeats and therefore is referred to as lipooligosaccharide (LOS) simply to reflect this fact (Schnaitman and Klena, supra; and Makela and Stocker, supra).

The biological properties of LPS have been extensively investigated (Rietschel et al, supra and Raetz, supra (1993)). This molecule has poweful pyrogenic properties and in humans ng quantities of LPS can induce febrile responses (Mackowiak (ed), supra; Greisman et al, supra; Abernathy and Spink, supra; Rietschel et al, supra; and Raetz, supra (1993)). These febrile responses are mediated by host proinflammatory cytokines IL-1, IL-6, and TNF-60, the secretion of which is induced by LPS (Mackowiak (ed), supra; Rietschel et al, supra and Raetz, supra).

The biologically active component of LPS is lipid A (Rietschel et al, supra; Verma et al, *Infect Immun*, 60(6) :2438–2444 (1992); Alving, *J Immunol Meth*, 140:1–13 (1991); Alving and Richards, *Immunol Lett*, 25:275–280) (1990); and Richard et al, *Infect Immun*, 56:682–686 (1988)). Activity analysis of lipid A biosynthesis precursors or synthetic intermediates showed that various elements of lipid A are essential for pyrgenicity (Rietschel et al, supra; Raetz, supra) Lipid X and lipid IVa are completely non-pyrogenic precursor forms of lipid A (Wang et al, *Infect Immun*, 59(12):4655–4664 (1991); Ulmer et al, *Infect Immun*, 60(12):145–5152 (1992); Kovach et al, *J Exp Med*, 172:77–84 (1990); Rietschel et al, supra; and Raetz, supra).

Lipid X is a monosaccharide precursor of lipid A (Rietschel et al, supra; and Raetz, supra (1993)). Lipid IVa, a tetraacyl precursor of lipid A, is interesting in that it retains the ability to bind to host cell surfaces but has no pyrogenicity, suggesting that binding to host cell surfaces per sa does not inpart this biological properties (Wang et al, *Infect Immun*, 59(12):4655–4664 (1991); Ulmer et al, *Infect Immun*, 60(12):145–5152 (1992); Kovach et al, *J Exp Med*, 172:77–84 (1990) and Rietschel et al, supra).

5. The Genetics of Lipid A Biosynthesis

The genetics of lipid A biosynthesis are well described (Raetz, supra; Raetz, *Ann Rev Biochem* 59:129–170 (1990);

and Schnaitman and Klena, supra). The majority of mutations that prevent the biosynthesis of lipid A, such as mutations in lpxA, lpxB, kdsA, kdsB, kdtA, are lethal as the biosynthesis of lipid A is essental for cell survival (Rick et al, *J Biol Chem*, 252:4904–4912 (1977); Rick and Osborn, *J Biol Chem*, 252:4895–4903 (1977); Raetz et al, *J Biol Chem*, 260:16080–16088 (1985); Raetz, supra (1990); Raetz, supra (1993); and Schnaitman and Klena, supra). For the most part, therefore, analysis of these genes has involved the use of temperature-sensitive mutants, which only display null phenotypes under non-permissive conditions (Rick et al, supra; Rick and Osborn, supra; Raetz et al, supra; Raetz, supra (1990); Raetz, supra (1993); and Schnaitman and Klena, supra). When grown under non-permissive conditions, lpxB, kdsA, kdsB, kdtA mutants accumulate non-pyrogenic precursor forms of LPS (to about 50% of the total LPS), such as lipid X (also called 2,3-diacyl-glucosamine-1-phosphate) or lipid IVa. Conditional-mutations in kdsA and kdsB prevent the biosynthesis of 3-deoxy-D-manno-octulsonic acid (KDO) and conditional-mutations in kdtA prevent the transfer of KDO to lipid IVa (Rick et al, supra; Rick and Osborn, supra; Raetz et al, supra; Raetz, supra (1990); Raetz, supra (1993); and Schnaitman and Klena, supra). The absence of KDO moieties on lipid IVa prevents further acylation of lipid IVa resulting in the accumulation of this molecule when KDO synthesis is blocked. The necessity to add KDO to lipid IVa prior to completion of lipid A biosynthesis is further demonstrated by the fact that drugs designed to block KDO synthesis are highly toxic to gram negative bacteria (Rick et al, supra; Rick and Osborn, supra; Raetz et al, supra; Raetz, supra (1990); Raetz, supra (1993); and Schnaitman and Klena, supra). Conditional-mutations in the lpxA gene result in a 10-fold reduction of lipid A biosynthesis under non-permissive conditions by preventing transfer of β-hydroxymyristate to UDP-GlcNAc, thereby preventing the synthesis of uridyldiphosphate-2,3-diacyl-glucosamine. Mutations in lpxA cause rapid cessation of growth and therefore the LpxA protein is a potential target for drug therapy. Further conditional-lethal mutants in lipid A biosynthesis also include lpxC and lpxD (Raetz, supra (1993)), which are necessary for the biosynthesis of uridyldiphosphate-2,3-diacyl-glucosamine. Recent evidence showing that ssc mutants (analogous to lpxD) of *Salmonella typhimurium* accumulate a pentaacyl form of lipid A indicates that this gene is also involved in lipid A biosynthesis.

There is indirect evidence that mutations in htrB and msb may influence the biosynthesis of lipid A (Karow et al, *J Bacteriol* 173:741–750 (1991); Karow and Georgopoulos, *J Bacteriol* 174:702–710 (1992)). These mutants are temperature sensitive and LPS isolated from these mutants stains less intensely on silver-stain gels (Karow and Geogopoulos, supra). The basis for the temperature-sensitive growth phenotype of the htrB and msb mutants has remained criptic (Karow and Geogopoulos, supra). There has been speculation that these mutants produce defective lipid A precursors (Karow and Geogopoulos, supra). This was based on the observation that ammonium cationic compounds enabled these mutants to grow in non-permissive temperatures (Karow and Geogopoulos, supra). These investigators proposed that the ammonium cationic compounds influenced the intermolecular interation between LPS molecules in the outer membrane. This observation is supported by recent data showing that an htrB mutant of *Hemophillus influenzae* produces modified LOS structures (Lee et al, *Infect Immun* 63:818–824 (1995); Lee at al, In: *Abstracts of the American Society for Microbiology*, ASM Washington D.C., p206(B-234) (1995)).

However, none of these investigators provided any direct evidence that htrB and msb mutants could produce substantially pure non-pyrogenic LPS. More importantly, these investigators did not show that these mutants would have the surprisingly broad biotechnology applications described herein.

6. Summary of the Background

There is a need for non-pyrogenic bacterial host strains that can be used to produce non-pyrogenic DNA, proteins, polysaccharides, vaccines, and vaccine vectors. The present invention describes a novel and unexpected finding that gram negative bacterial mutants can be continuously grown in the presence of quaternary cationic compounds under non-permissive growth conditions and accumulate substantially pure non-pyrogenic lipid A precursors.

SUMMARY OF THE INVENTION

An object of the present invention is to provide a novel and simple method for culturing mutant bacterial strains so that said mutants produce substantially pure non-pyrogenic lipid A or LPS.

An additional object of the present invention is to provide a method for preparing non-pyrogenic DNA.

Another object of the present invention is to use non-pyrogenic DNA to deliver one or more eukaryotic expression cassettes to animal cells or animal tissue.

Yet another object of the present invention is to use non-pyrogenic DNA to deliver one or more eukaryotic expression cassettes encoding a vaccine antigen(s) to animal cells or animal tissue.

Still another object of the present invention is to use non-pyrogenic DNA to deliver one or more eukaryotic expression cassettes encoding gene therapeutic agents to animal cells or animal tissue.

A further objective of the present invention is to use non-pyrogenic DNA to deliver one or more eukaryotic expression cassettes encoding biologically active RNA species to animal cells or animal tissue.

An object of the present invention is to provide a novel and simple method for preparing non-pyrogenic recombinant mammalian, protozoan and viral proteins.

Another object of the present invention is to use non-pyrogenic proteins as a therapeutic agents in animal cells or animal tissue.

Yet another object of the present invention is to use non-pyrogenic proteins as a immunotherapeutic agents in animal cells or animal tissue.

Still a further object of the present invention is to use non-pyrogenic proteins and polysaccharides as vaccines in animal cells or animal tissue.

Another object of the present invention is to provide non-pyrogenic bacterial vaccines against typhoid fever, cholera, shigellosis, diarrheagenic *Escherichia coli*, pathogenic Yersinia, pathogenic Mycobacterium, pathogenic Neiseria, pathogenic Bordetella, pathogenic Aeromonas, pathogenic Corynebacterium, pathogenic Hemophilus, pathogenic Brucella, and pathogenic Helicobacter.

Still another object of the present invention is to provide non-pyrogenic oral bacterial vaccines against Salmonella spp., Vibrio spp., Shigella spp., diarrheagenic *Escherichia coli*, pathogenic Yersinia, pathogenic Mycobacterium, pathogenic Neiseria, pathogenic Bordetella, pathogenic Aeromonas, pathogenic Corynebacterium, pathogenic Hemophilus, pathogenic Brucella, and pathogenic Helicobacter.

Yet another object of the present invention is to provide non-pyrogenic bacterial vaccines which predominantly induce type 2 $T_{helper}$ lymphocyte responses and mucosal secretory IgA responses against Salmonella spp., Vibrio spp., Shigella spp., diarrheagenic *Escherichia coli*, pathogenic Yersinia, pathogenic Mycobacterium, pathogenic Neiseria, pathogenic Bordetella, pathogenic Aeromonas, pathogenic Corynebacterium, pathogenic Hemophilus, pathogenic Brucella, and pathogenic Helicobacter.

Yet another object of the present invention is to is provide non-pyrogenic bacterial vaccine vectors which are useful as a carrier of genes expressing foreign antigens cloned from other viral, parasitic and bacterial pathogens and that raises protective immune responses against the pathogen from which the foreign antigens were derived.

Yet another object of the present invention is to provide non-pyrogenic bacterial vaccine vectors which induce type 2 $T_{helper}$ lymphocyte responses and mucosal secretory IgA responses.

These and other objects of the present invention, which will be apparent from the detailed description of the invention provided hereinafter, have been met in one embodiment by a method for isolating non-pyrogenic bacterial strains and in further embodiments describing the use of said non-pyrogenic strains for the production of DNA, recombinant proteins, vaccines and vaccine vectors.

DETAILED DESCRIPTION OF THE INVENTION

1. Preparation of Non-pyrogenic Bacteria

As discussed above, in one embodiment, the present invention provides a culturing method that allows mutant bacterial strains to produce substantially pure non-pyrogenic lipid A or LPS.

We have found that gram negative bacterial strains, which contain a conditional mutation (or mutations) that results in the accumulation of lipid A precursors, are capable of exclusively producing non-pyrogenic LPS (ie. LPS that is $10^7$-fold less toxic than wild type LPS) under specific growth conditions in supplemented culture medium.

Examples of such conditional mutations that affect the biosynthesis of lipid A and result in the accumulation of non-pyrogenic LPS include, but are not restricted to, mutations in htrB, mstB, kdsA, kdsB, and kdtA (Rick et al, supra; Rick and Osborn, supra; Raetz et al, supra; Raetz, supra (1990); Raetz, supra (1993); Schnaitman and Klena, supra; Lee et al, *Infect Immun*, 63(3):818–824 (1995); Karow and Georgopoulos, *Molec Microbiol*, 5(91:2285–2292 (1991); and Karow et al *J Bacteriol*, 173(2):741–750 (1991)). These mutations could be introduced alone. Alternatively, any combination of mutations in the kdsA, kdsB, lpxB, kdtA, lpxC (synonym is envA), lpxD(synonyms are firA and ssc), ssc, lpxA, htrB, and the msbB genes (Rick et al, supra; Rick and Osborn, supra; Raetz et al, supra; Raetz, supra (1990); Raetz, supra (1993); and Schnaitman and Klena, supra; Lee et al, supra; Karow and Georgopoulos, supra; Karow and Georgopoulos, *J Bacteriol*, 174:702–710 (1992); and Karow et al, supra), which may affect the biosynthesis of lipid A and result in the synthesis of non-pyrogenic lipid A structures could be used.

These mutations can be introduced into gram negative bacteria using non-specific mutagenesis either chemically, using agents such as N-methyl-N'-nitro-N-nitrosoguanidine, or using recombinant DNA techniques; classic genetic techniques, such as Tn10 mutagenesis, bacteriophage-mediated transduction, lambda phage-mediated crossover, and conjugational transfer; or site-directed mutagenesis using recombinant DNA techniques. Recombinant DNA techniques are preferable since strains constructed by recombinant DNA techniques are far more defined and less likely to revert. The mutations can be either constitutively expressed or under the control of inducible promoters, such as the temperature sensitive heat shock family of promoters (Neidhardt et al, supra), or the anaerobically-induced nirB promoter (Harborne et al, *Mol. Micro.*, 6:2805–2813 (1992)) or repressible promoters, such as uapA (Gorfinkiel et al, *J. Biol. Chem.*, 268:23376–23381 (1993)) or gcv (Stauffer et al, *J. Bact.*, 176:6159–6164 (1994)).

These mutations can be introduced in conjunction with one or more additional mutations. Examples of such additional mutations include, but are not limited to:

(i) auxotrophic mutations, such as aro (Hoiseth et al, *Nature*, 291:238–239 (1981)), gua (McFarland et al, *Microbiol. Path.*, 3:129–141 (1987)), and (Park et al, *J. Bact.*, 170:3725–3730 (1988), thy (Nnalue et al, *Infect. Immun.*, 55:955–962 (1987)), and asd (Curtiss, supra) mutations;

(ii) mutations that inactivate global regulatory functions, such as cya (Curtiss et al, *Infect. Immun.*, 55:3035–3043 (1987)), crp (Curtiss et al (1987), supra), phoP/phoQ (Groisman et al, *Proc. Natl. Acad. Sci., USA*, 86:7077–7081 (1989); and Miller et al, *Proc. Natl. Acad. Sci., USA*, 86:5054–5058 (1989)), phoP$^c$ (Miller et al, *J. Bact.*, 172:2485–290 (1990)) or ompR (Dorman et al, *Infect. Immun.*, 57:2136–2140 (1989)) mutations;

(iii) mutations that modify the stress response, such as recA (Buchmeier et al, *Mol. Micro.*, 7:933–936 (1993)), htrA (Johnson et al, *Mol. Micro.*, 5:401–407 (1991)), htpR (Neidhardt et al, *Biochem. Biophys. Res. Com.*, 100:894–900 (1981)), hsp (Neidhardt et al, *Ann. Rev. Genet.*, 18:295–329 (1984)) and groEL (Buchmeier et al, *Sci.*, 248:730–732 (1990)) mutations;

(iv) mutations in specific virulence factors, such as lsyA (Libby et al, *Proc. Natl. Acad. Sci., USA*, 91:489–493 (1994)), paq or prg (Miller et al (1990), supra; and Miller et al (1939), supra), iscA or virG (d'Hauteville et al, *Mol. Micro.*, 6:833–841 (1992)), picA (Mengaud et al, *Mol. Microbiol.*, 5:367–72 (1991); Camilli et al, *J. Exp. Med*, 173:751–754 (1991)), and act (Brundage et al, *Proc. Natl. Acad. Sci., USA*, 90:11890–11894 (1993)) mutations;

(v) mutations that affect DNA topology, such as topA (Galan et al, *Infect. Immun.*, 58:1879–1885 (1990)) mutation;

(vi) mutations that alter the biogenesis of surface polysaccharides, such as rfb, galE (Hone et al, *J. Infect. Dis.*, 156:164–167 (1987)) or via (Popoff et al, *J. Gen. Microbiol.*, 138:297–304 (1992)) mutations;

(vii) mutations that modify suicide systems, such as sacB (Recorbet et al, *App. Environ. Micro.*, 59:1361–1366 (1993); Quandt et al, *Gene*, 127:15–21 (1993)), nuc (Ahrenholtz et al, *App. Environ. Micro.*, 60:3746–3751 (1994)), hok, gef, kil, or phiA (Molin et al, *Ann. Rev. Microbiol.*, 47:139–166 (1993)) mutations;

(viii) mutations that introduce suicide systems, such as lysogens encoded by P22 (Rennell et al, *Virol.*, 143:280–289 (1985)), λ murein transglycosylase (Bienkowska-Szewczyk et al, *Mol. Gen. Genet.*, 184:111–114 (1981)) or S-gene (Reader et al, *Virol.*, 43:623–628 (1971)); and (ix) mutations that disrupt or modify the correct cell cycle, such as minC (de Boer et al, *Cell*, 56:641–649 (1989)) mutation.

(x) mutations that change the restriction-modification phenotype, such as deo, mcr, hsdR and hsdM (Grant et al, supra).

Normally, exclusive expression of lipid A precursors is toxic to the bacterium. Thus, when these mutants are grown in non-permissive conditions, whereby lipid A precursors accumulate, the bacteria usually only undergo a single division before ceasing to grow. For example, in certain lipid A-defective mutants expression of lipid IVa (a tetracyl precursor of lipid A) can only reach levels of 30–50% of the total LPS before growth of the strain ceases (Rick ad Osborn, supra, Raetz, supra (1993)).

However, surprisingly growth of the conditional-mutants that produce lipid A precursors in non-permissive conditions, ie. at 35° C. to 44° C., in the presence of quaternary cationic compounds, suppresses the conditional-lethal affect of these mutations and allows the accumulation of non-pyrogenic LPS/lipid A precursors. Thus, under these culture conditions the bacteria continue to grow and accumulate substantially pure (>99%) non-pyrogenic LPS.

The particular quaternary cationic compound used is not critical to the current invention; examples include tetraa-cyltetramethylammonium bromide (herein TTAB; Sigma, St Lous Mo., USA), polylysine (Sigma), polymyxin (Sigma), ethanolamine (Sigma) dimethyldictadecylammonium bromide (DDAB from ICN, Costa Mesa, Calif., USA), 1,2, diacyl-3-trimethylammonium-propane (TAP; Avanti Polar Lipids Inc, Ala., USA), 2,-dioleyloxy-N-[2 (perminecarboxamindo)-ethyl]-N,N-dimethyl-1-propanammoniumtrifluoroacetate (DOSPA; GibcoBRL, Gaithersburg, Md., USA), and N-[1-2,3-dioleyloxy)propyl]-N,N,N-trimethylammonium chloride (DOTMA; GibcoBRL, supra).

The concentration of the quaternary cationic compound in the medium is not critical to the present invention but usually is a concentration that is sublethal to the bacterial strain, ranging from 0.01 $\mu$g/ml to 100 $\mu$g/ml. The concentration of quaternary cationic compound chosen will depend on the bacterial species and genotype and can be identified by growing the mutant organism at permissive and non-permissive temperatures in the presence of the said range. The quaterary cationic compound can be added to liquid media, such as Luria-Bertani (LB) broth, Difco Nutrient broth, Difco Brain Heart infusion broth or M9 minimal broth, or solid media such as LB agar, Difco Nutrient agar, Difco Brain Heart infusion agar or M9 minimal agar.

The non-pyrogenic bacteria can be cultured at temperatures ranging from 35° C. to 44° C. Culturing can occur with or without agitation. Additional oxygen can be introduced into the culture using agitation or by direct injection of oxygen gas in a liquid fermentor. The optical density at 600 nm at which the non-pyrogenic cells are harvested is not critical thereto, and can range from 0.1 to 5.0 and will be dependent on the specific media culture conditions employed.

The particular non-pyrogenic lipid A-producing bacteria employed in the present invention is not critical thereto and could be any gram negative bacterium. Examples of such gram-negative bacteria include, but are not limited to, Escherichia spp, Shigella spp, Salmonella spp, Campylobacter spp, Neiseria spp., Haemophilus spp, Aeromonas spp, Franciesella spp, Yersinia spp, Klebsiella spp, Bordetella spp, Legionella spp, Corynebacterium spp, Citrobacter spp, Chlamydia spp, Brucella Spp, Pseudomonas spp, Helicobacter spp, or Vibrio spp.

The particular Escherichia strain employed is not critical to the present invention. Examples of Escherichia strains which can be employed in the present invention include *Escherichia coli* strains DH5 $\alpha$, HB 101, HS-4, 4608-58, 1184-68, 53638-C-17, 13-80, and 6-81 (Sambrook et al, supra; Grant et al, supra; Sansonetti et al, *Ann. Microbiol.* (Inst. Pasteur), 132A:351–355 (1982)), enterotoxigenic *E. coli* (Evans et al, *Infect Immun* 12:656–667 (1975)), enteropathogenic *E. coli* (Donnenberg et al, *J. Infect. Dis.*, 169:831–838 (1994)) and enterohemoragenic *E. coli* (McKee and O'Brien, *infect Immun* 63:2070–2074 (1995)).

The particular Shigella strain employed is not critical to the present invention. Examples of Shigella strains which can be employed in the present invention include *Shigella flexneri* (ATCC No. 29903), *Shigella sonnei* (ATCC No. 29930), and *Shigella disenteriae* (ATCC No. 13313).

The particular Campylobacter strain employed is not critical to the present invention. Examples of Campylobacter strains which can be employed in the present invention include but are not limited to *C. jujuni* (ATCC Nos. 43436, 43437, 43438), *C. hyointestinalis* (ATCC No. 35217), *C fetus* (ATCC No. 19438) *C. fecalis* (ATCC No. 33709) *C. doylei* (ATCC No. 49349) and *C. coli* (ATCC Nos. 33559, 43133).

The particular Yersinia strain employed is not critical to the present invention. Examples of Yersinia strains which can be employed in the present invention include *Y. enterocolitica* (ATCC No. 9610) or *Y. pestis* (ATCC No. 19428), *Y. enterocolitica* Ye03-R2 (al-Hendy et al, *Infect. Immun.*, 60:870–875 (1992)) or *Y. enterocolitica* aroA (O'Gaora et al, *Micro. Path.*, 9:105–116 (1990)).

The particular Klebsiella strain employed is not critical to the present invention. Examples of Klebsiella strains which can be employed in the present invention include *K. pneuoniae* (ATCC No. 13884).

The particular Bordetella strain employed is not critical to the present invention. Examples of Bordetella strains which can be employed in the present invention include *B. purtussis, B. bronchiseptica* (ATCC No. 19395).

The particular Neisseria strain employed is not critical to the present invention. Examples of Neisseria strains which can be employed in the present invention include *N. meningitidis* (ATCC No. 13077) and *N. gonorrhoeae* (ATCC No. 19424), *N. gonorrhoeae* MS11 aro mutant (Chamberlain et al, *Micro. Path.*, 15:51–63 (1993)).

The particular Aeromonas strain employed is not critical to the present invention. Examples of Aeromonas strains which can be employed in the present invention include *A. salminocida* (ATCC No. 33658), *A. schuberil* (ATCC No. 43700), *A. hydrophila, A. eucrenophila* (ATCC No. 23309).

The particular Franciesella strain employed is not critical to the present invention. Examples of Franiesella strains which can be employed in the present invention include *F. tularensis* (ATCC No. 15482).

The particular Corynebacterium strain employed is not critical to the present invention. Examples of Corynebacterium strains which car be employed in the present invention include *C. pseudotuberculosis* (ATCC No. 19410).

The particular Citrobacter strain employed is not critical to the present invention. Examples of Citrobacter strains which can be employed in the present invention include *C. freundii* (ATCC No. 8090).

The particular Chlamydia strain employed is not critical to the present invention. Examples of Chlamydia strains which can be employed in the present invention include *C. pneumonia* (ATCC No. VR1310).

The particular Hemophilus strain employed is not critical to the present invention. Examples of Hemophilus strains which can be employed in the present invention include *H. influenza* (Lee et al, surpa), *H. sornnus* (ATCC No. 43625).

The particular Brucella strain employed is not critical to the present invention. Examples of Brucella strains which can be employed in the present invention include *B. abortus* (ATCC No. 23448).

The particular Legionella strain employed is not critical to the present invention. Examples of Legionella strains which can be employed in the present invention include *L. pneumophila* (ATCC No. 33156), or a *L. pneumophila* mip mutant (Ott, *FEMS Micro. Rev.*, 14:161–176 (1994)).

The particular Pseudomonas strain employed is not critical to the present invention. Examples of Pseudomonas strains which can be employed in the present invention include *P. aeruginosa* (ATCC No. 23267).

The particular Helicobacter strain employed is not critical to the present invention. Examples of Helicobacter strains which can be employed in the present invention include *H. pylori* (ATCC No. 43504), *H. mustelae* (ATCC No. 43772).

The particular Salmonella strain employed is not critical to the present invention. Examples of Salmonella strains which can be employed in the present invention include *S. typhi* (ATCC No. 7251), *S. typhimurium* (ATCC No. 13311), *Salmonella galinarum* (ATCC No. 9184), *Salmonella enteriditis* (ATCC No. 4931) and *Salmonella typhimurium* (ATCC No. 6994). *S. typhi* aroC, aroD (Hone et al, *Vacc.*, 9:810–816 (1991)), *S. typhimurium* aroA mutant (Mastroeni et al, *Micro. Pathol.*, 13:477–491 (1992)).

The particular Vibrio strain employed is not critical to the present invention. Examples of Vibrio strains which can be employed in the present invention include *Vibrio cholerae* (ATCC No. 14035) *Vibrio cincinnatiensis* (ATCC No. 35912), *V. cholerae* RSI virulence mutant (Taylor et al, *J. Infect. Dis.*, 170:1518–1523 (1994)) and *V. cholera* ctxA, ace, zot, cep mutant (Waldor et al, *J. Infect. Dis.*, 170:278–283 (1994)).

2. Preparation of Non-pyrogenic DNA

As discussed above, in another embodiment, the present invention relates to a method for preparing non-pyrogenic DNA and use of the same for introducing DNA containing a eukaryotic expression cassette encoding a gene into animal cells and expressing said gene in animal cells.

Preparation of non-pyrogenic DNA genetic elements that encode the eukaryotic expression cassettes from strains that produce substantialy pure non-pyrogenic LPS is conducted under Good Laboratory Practice (GLP) or Good Manufacturing Practice (GMP) conditions (Smith, supra). First, the DNA genetic elements (eg. plasmid, cosmid, phagemid, bacteriophage (Sambrook et al (eds), supra)) that encode the eukaryotic expression cassettes of interest is introduced into said non-pyrogenic bacterial strain by standard bacterial transformation, transduction, or conjugation techniques (Miller (ed) In: *Experiments in Molecular Genetics*, Cold Spring Harbor Press, Cold Spring Harbor, N.Y. (1972); and Sambrook et al (eds), supra). The non-pyrogenic bacterial strain containing said genetic element is then cultured to produce substantially pure non-pyrogenic LPS as outlined above. Then, said genetic element can be isolated and purified from the transformants by well-known DNA isolation techniques such as alkaline lysis (Sambrook et al (eds), supra), detergent lysis (Sambrook et al (eds), supra), heat lysis (Sambrook et al (eds), supra), enzymatic lysis (Sambrook et al (eds), supra), the Qiagen$^R$ purification kit (Qiagen Inc, Chatsworth Calif.), $CsCl_2$ density gradients (Sambrook et al (eds), supra) or a combination of any of these preparative techniques. This DNA may be sufficiently pure to perform veterinary immunizations or gene delivery procedures. However, for work in humans additional purification may be necessary (Smith, supra)

To further purifiy the genetic element, the genetic element can be precipitated with organic solvents such as isopropanol or ethanol (Sambrook et al (eds), supra), resuspended in a pharmacologically acceptable, pyrogenc-free, and commercially available (Life Technologies) diluent such as PBS, N-saline or citrate buffer, filter-sterilized (eg. pass the genetic element through a commercially-available 0.1 $\mu$m filter (Milipore)) and dialysed (eg. using dialysis tubing with a molecular weight cut-off of >100 kD) against the same diluent to remove any low molecular weight contaminants. Purity of the non-pyrogenic DNA can be examined spectrophotometrically (Sambrook et al (eds), supra).

Having prepared the non-pyrogenic DNA as outlined above, it could be formulated as naked DNA (Smith supra), into liposomes, proteosomes or protein cochleates (Pinnaduwage et al, supra; Len et al, *Biochim Biophys Acta*, 981:27–35 (1989); Gershonet al, *Biochem*, 32:7143–7151 (1993); Felger et al, supra; Hug and Sleight, supra; and New (ed), In: *Liposomes*, IRL Press, Oxford England (1990)) and delivered to animal cells in vitro or to animal cells in animal tissue. The route of delivery will vary depending on the formulation, the gene being delivered and the target cell type, but could be any one of the intravenous, intramuscular, intradermal, intra-peritoneal, intra-nasal intraocular, intrarectal intravaginal, oral, and intraurethral inoculation routes.

Animal cells are defined as nucleated, non-chloroplast containing cells derived from or present in multicellular organisms whose taxanomic position lies within the kingdom animalia. The cells may be present in the intact animal, a primary cell culture, explant culture or a transformed cell line. The particular tissue source of the cells is not critical to the present invention.

The recipient animal cells employed in the present invention are not critical thereto and include cells present in or derived from all organisms within the kingdom animalia, such as those of the families mammalia, pisces, avian, reptilia.

Preferred animal cells are mammalian cells, such as humans, bovine, ovine, porcine, feline, buffalo, canine, goat, equine, donkey, deer, and primate cells. The most preferred animal cells are human cells.

Examples of human cell lines include but are not limited to ATCC Nos. CCL 62, CCL 159, HTB 151, HTB 22, CCL 2, CRL 1634, CRL 8155, HTB 61, and HTB104.

Examples of bovine cell lines include ATCC Nos. CRL 6021, CRL 1733, CRL 6033, CRL 6023, CCL 44 and CRL 1390.

Examples of ovine cells lines include ATCC Nos. CRL 6540, CRL 6538, CRL 6548 and CRL 6546.

Examples of porcine cell lines include ATCC Nos. CL 184, CRL 6492, and CRL 1746.

Examples of feline cell lines include ATCC Nos. CRL 6077, CRL 6113, CRL 6140, CRL 6164, CCL 94, CCL 150, CRL 6075 and CRL 6123.

Examples of buffalo cell lines include ATCC Nos. CCL 40 and CRL 6072.

Examples of canine cells include ATCC Nos. CRL 6213, CCL 34, CRL 6202, CRL 6225, CRL 6215, CRL 6203 and CRL 6575.

Examples of goat derived cell lines include ATCC No. CCL 73 and ATCC No. CRL 6270.

Examples of horse derived cell lines include ATCC Nos. CCL 57 and CRL 6583.

Examples of deer cell lines include ATCC Nos. CRL 6193–6196.

Examples of primate derived cell lines include those from chimpanzee's such as ATCC Nos. CRL 6312, CRL 6304, and CRL 1868; monkey cell lines such as ATCC Nos. CRL 1576, CCL 26, and CCL 161; orangautan cell line ATCC No. CRL 1850; and gorilla cell line ATCC No. CRL 1854.

As discussed above, the recipient animal cells to which non-pyrogenic DNA delivers a eukaryotic expression cassette may be those derived from fish, birds or reptiles.

The particular eukaryotic cassette employed in the present invention is not critical thereto, and can be selected from, e.g., any of the many commercially available cassettes, such as pCEP4 or pRc/RSV obtained from Invitrogen Corporation (San Diego, Calif.), pXT1, pSG5 obtained from Stratagene (La Jolla, Calif.), pPUR or pMAM obtained from ClonTech (Palo Alto, Calif.), and pSVβ-gal obtained from Promega Corporation (Madison, Wis.), or synthesized either de novo or by adaptation of a publically or commercially available eukaryotic expression system.

The individual elements within the eukaryotic expression cassette can be derived from multiple sources and may be selected to confer specificity in sites of action or longevity of the cassettes in the recipient cell. Such manipulation of the eukaryotic expression cassette can be done by any standard molecular biology approach.

These cassettes usually are in the form of genetic elements (eg. plasmid, cosmid, phagemid, bacteriophage (Sambrook et al (eds), supra)) and contain various promoters well-known to be useful for driving expression of genes in animal cells, such as the viral derived SV40, CMV, MMLV, MMTV, EBV, HIV, LTR, and RSV promoters or eukaryotic derived β-casein, uteroglobin β-actin or tyrosinase promoters. The particular promoter is not critical to the present, except in the case where the object is to obtain expression in only selective cell types. In this case, the promoter is selected to be one which is only active in the selected cell type. Examples of tissue specific promoters include, but are not limited to, αS1- and β-casein promoters which are specific for mammary tissue (Platenburg et al, *Trans. Res.*, 3:99–108 (1994); and Maga et al, *Trans. Res.*, 3:36–42 (1994)); the phosphoenolpyruvate carboxykinase promoter which is active in liver, kidney, adipose, jejunum and mammary tissue (McGrane et al, *J. Reprod. Fert.*, 41:17–23 (1990)); the tyrosinase promoter which is active in lung and spleen cells, but not testes, brain, heart, liver or kidney (Vile et al, *Canc. Res.*, 54:6228–6234 (1994)); the involucerin promoter which is only active in differentiating keratinocytes of the squamous epithelia (Carroll et al, *J. Cell Sci.*, 103:925–930 (1992)); and the uteroglobin promoter which is active in lung and endometrium (Helftenbein et al, *Annal. N.Y. Acad. Sci.*, 62:69–79 (1991)).

Alternatively, cell specific enhancer sequences can be used to control expression, for example human neurotropic papovirus JCV enhancer regulates viral transcription in glial cells alone (Remenick et al, *J. Virol.*, 65:5641–5646 (1991)). Yet another way to control tissue specific expression is to use a hormone responsive element (HRE) to specify which cell lineages a promoter will be active in, for example, the MMTV promoter requires the binding of a hormone receptor, such as progesterone receptor, to an upstream HRE before it is activated (Beato, *FASEB J.*, 5:2044–2051 (1991); and Truss et al, *J. Steroid Biochem. Mol. Biol.*, 41:241–248 (1992)).

Additional genetic elements may be included on the plasmid in order to modify its behavior inside the recipient animal cell (Hodgson, *Bio/Technology*, 13:222–225 (1995)). Such elements include but are not limited to mammalian artificial chromosome elements or elements from the autonomous replicating circular minichromosomes, such as found in DiFi colorectal cancer cells, to allow stable non-integrated retention of the expression cassette (Huxley et al, *Bio/Technology*, 12:586–590 (1994); and Untawale et al, *Canc. Res.*, 53:1630–1636 (1993)), intergrase to direct integration of the expression cassette into the recipient cells chromosome (Bushman, *Proc. Natl. Acad. Sci., USA*, 91:9233–9237 (1994), the inverted repeats from adeno-associated virus to promote non-homologous integration into the recipient cells chromosome (Goodman et al, *Blood*, 84:1492–1500 (1994), recA or a restriction enzyme to promote homologous recombination (PCT Patent Publication No. WO9322443 (1993); and PCT Patent Publication No. WO9323534-A (1993)) or elements that direct nuclear targeting of the eukaryotic expression cassette (Hodgson, supra; and Lewin, supra).

In the present invention, non-pyrogenic DNA can deliver eukaryotic expression cassettes encoding a gene into an animal cell or animal tissue. The gene may be either a foreign gene or a endogenous gene. As used herein, "foreign gene" means a gene encoding a protein or fragment thereof or anti-sense RNA or catalytic RNA, which is foreign to the recipient animal cell or tissue, such as a vaccine antigen, immunoregulatory agent, or therapeutic agent. An "endogenous gene" means a gene encoding a protein or part thereof or anti-sense RNA or catalytic RNA which is expected to be naturally present in the recipient animal cell or tissue.

The vaccine antigen may be a protein or antigenic fragment thereof from viral pathogens, bacterial pathogens, and parasitic pathogens. Alternatively, the vaccine antigen may be a synthetic gene, constructed using recombinant DNA methods, which encode antigens or parts thereof from viral, bacterial, parasitic pathogens. These pathogens can be infectious in humans, domestic animals or wild animal hosts.

The antigen can be any molecule that is expressed by any viral, bacterial, parasitic pathogen prior to or during entry into, colonization of, or replication in their animal host.

Multiple eukaryotic expression cassettes can be delivered that express any combination of viral, bacterial, parasitic antigens, or synthetic genes encoding all or parts or any combination of viral, bacterial, parasitic antigens.

The viral pathogens, from which the viral antigens are derived, include, but are not limited to, Orthomyxoviruses, such as influenza virus; Retroviruses, such as RSV and SIV, Herpesviruses, such as EBV; CMV or herpes simplex virus; Lentiviruses,such as human immunodeficiency virus; Rhabdoviruses, such as rabies; Picornoviruses, such as poliovirus; Poxviruses, such as vaccinia; Rotavirus; Papalomavirus and Parvoviruses.

Examples of protective antigens of viral pathogens include the human immunodeficiency virus antigens Nef, Gag, p24, gp120, gp41, Tat, Rev, and Pol (Wang-Staal et al, *Nature*, 313:277–280 (1985)) and T cell and B cell epitopes of gp120 (Palker et al, *J. Immunol.*, 142:3612–3619 (1989)); the hepatitis B core and surface antigens (Wu et al, *Proc. Natl. Acad. Sci., USA*, 86:4726–4730 (1989)); rotavirus antigens, such as VP4 (Mackow et al, *Proc. Natl. Acad. Sci., USA*, 87:518–522 (1990)) and VP7 (Green et al, *J. Virol.*, 62:1819–1823 (1988)), influenza virus antigens such as hemagglutinin or nucleoprotein (Robinson et al., Supra; Webster et al, Supra) and herpes simplex virus thymidine kinase (Whitley et al, In: *New Generation Vaccines*, pages 825–854).

The bacterial pathogens, from which the bacterial antigens are derived, include but are not limited to, Mycobacterium spp., *Helicobacter pylori*, Salmonella spp., Shigella spp., *E. coli*, Rickettsia spp., Listeria spp., *Legionella pneumoniae*, Pseudomonas spp., *Vibrio* spp., and *Borellia burgdorferi*.

Examples of protective antigens of bacterial pathogens include the *Shigella sonnei* form 1 antigen (Formal et al, supra); the O-antigen of *V. cholerae* Inaba strain 569B (Forrest et al, *J. Infect. Dis.*, 159:145–146 (1989); protective antigens of enterotoxigenic *E. coli*, such as the CFA fimbrial antigens (Yamamoto et al, *Infect. Immun.*, 50:925–928 (1985)) and the nontoxic B-subunit of the heat-labile toxin (Clements et al, 46:564–569 (1984)); pertactin of *Bordetella pertussis* (Roberts et al, Vacc., 10:43–48 (1992)), adenylate cyclase-hemolysin of *B. pertussis* (Guiso et al, *Micro. Path.*, 11:423–431 (1991)), and fragment C of tetanus toxin of *Clostridium tetani* (Fairweather et al, *Infect. Immun.*, 58:1323–1326 (1990)).

The parasitic pathogens, from which the parasitic antigens are derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp.

Examples of protective antigens of parasitic pathogens include the circumsporozoite antigens of Plasmodium spp. (Sadoff et al, *Science*, 240:336–337 (1988)), such as the circumsporozoite antigen of *P. bergerii*, *P. falciparum* or *P. vivax*; the merozoite surface antigens of Plasmodium spp. (Spetzler et al, *Int. J. Pept. Prot. Res.*, 48:351–358 (1994)); the liver stage antigens of *P. falciparum* (Guerin-Marchand et al, Nature(London), 329:164–167 (1987)); the galactose specific lectin of *Entamoeba histolytica* (Mann et al, *Proc. Natl. Acad. Sci., USA*, 88:3248–3252 (1991)), gp63 of Leishmania spp. (Russell et al, *J. Immunol.*, 140:1274–1278 (1988)), paramyosin of Brugia malayi (Li et al, *Mol. Biochem. Parasitol.*, 49:315–323 (1991)), the triose-phosphate isomerase of *Schistosoma mansoni* (Shoemaker et al, *Proc. Natl. Acad. Sci., USA*, 89:1842–1846 (1992)); the secreted globin-like protein of *Trichostrongylus colubriformis* (Frenkel et al, *Mol. Biochem. Parasitol.*, 50:27–36 (1992)); the glutathione-S-transferase's of *Fasciola hepatica* (Hillyer et al, *Exp. Parasitol.*, 75:176–186 (1992)), *Schistosoma bovis* and *S. japonicum* (Bashir et al, *Trop. Geog. Med.*, 46:255–258 (1994)); and KLH of *Schistosoma bovis* and *S. japonicum* (Bashir et al, supra).

In the present invention, the non-pyrogenic DNA can also deliver eukaryotic expression cassettes encoding a therapeutic agent to animal cells or animal tissue. For example, the eukaryotic expression cassettes can encode tumor-specific, transplant, or autoimmune antigens or parts thereof. Alternatively, the eukaryotic expression cassettes can encode synthetic genes, which encode tumor-specific, transplant, or autoimmune antigens or parts thereof.

Examples of tumor specific antigens include prostate specific antigen (Gattuso et al, *Human Pathol.*, 26:123–126 (1995)), TAG-72 and CEA (Guadagni et al, *Int. J. Biol. Markers*, 9:53–60 (1994)), MAGE-1 and tyrosinase (Coulie et al, *J. Immunother.*, 14:104–109 (1993)). Recently it has been shown in mice that immunization with non-malignant cells expressing a tumor antigen provides a vaccine effect, and also helps the animal mount an immune response to clear malignant tumor cells displaying the same antigen (Koeppen et al, *Anal. N.Y. Acad. Sci.*, 690:244–255 (1993)).

Examples of transplant antigens include the CD3 receptor on T cells (Alegre et al, *Digest. Dis. Sci.*, 40:58–64 (1995)). Treatment with an antibody to CD3 receptor has been shown to rapidly clear circulating T cells and reverse most rejection episodes (Alegre et al, supra).

Examples of autoimmune antigens include IAS α-chain (Topham et al, *Proc. Natl. Acad. Sci., USA*, 91:8005–8009 (1994)). Vaccination of mice with an 18 amino acid peptide from IAS β-chain has been demonstrated to provide protection and treatment to mice with experimental autoimmune encephalomyelitis (Topham et al, supra).

In addition the non-pyrogenic DNA described herein can be used to deliver gene therapeutic agents or genes to recipient animal cells or animal tissue. Strategies for gene therapy currently include the genetic complementation of inherited or spontaneous genetic disorders, mutations, or deficits (Lisziewicz, *Leuk.*, 8:S152–155 (1994)), and the supplementation of genes in order to enhance or alter the dose of a particular encoded factor or enzyme. Genetic elements delivered in eukaryotic expression cassettes derived from non-pyrogenic bacterial host strains to complement a mutated or non-functional gene in the animal cell could encode an entire replacement gene, or set of related genes, a complimentary DNA sequence encoding a primary RNA transcript, partially or completely processed RNA transcript, trans- or cis-acting regulatory element, enhancer or other modulatory factor. In order to complement some genetic defects it may be necessary to deliver one or more eukaryotic expression cassette each encoding one or more components of a biochemical pathway. Individual or multi-enzyme components or gene therapeutic elements can be delivered individually or in combination with other gene or other eukaryotic expression cassettes.

The advent of increasingly more powerful molecular techniques has recently resulted in an exponential growth of information on genetic lessions and the disease states resulting from such lessions. An exhaustive list of currently known genetic lessions and resulting disease state is outside the scope or claim of this document. Diseases for which, currently, a specific genetic lession has been defined and potential in vitro or in vivo treatment(s) reported, and the gene or genes in which the genetic lessions occur include but are not limited to: cystic fibrosis transmembrane conductance regulator (Yoshimura et al., *Nuc. Acids Res.*, 20:3233–3240 (1992); Zabner et al., *Cell.* 75:207–216 (1993); Zabner et al,supra (1994); Caplen et al, supra); emphysema-α1 antitrypsin (Setoguchi et al., *Am. J. Resp. Cell. Molec. Biol.*, 10:369–377 (1994)); familial hypercholesterolaemia-LDL receptor (Grossman et al, *Nat. Genet.*, 6:335–341 (1994)); fanconi anemia-fanconi anemia C complementing gene (Walsh et al., *Blood*, 84:453–459 (1994)); hypertension-kallikrein gene (Wang et al., *J. Clin. Invest.*, 95:1710–1716 (1995)); mucopolysaccharidosis type II (Hunter syndrome)-iduronate-2-sulfatase (Braun et al., *Proc. Natl. Acad. Sci., USA*, 90:11830–11834 (1933)); propionyl coA carboxylase defficeny-PCCA (Stankovics and Ledley, *Am. J. Hum. Genet.*, 52:144–151 (1993)); Sly syndrome-beta-glucuronidase (Moullier et al, *Nat. Genet.*, 4:154–159 (1993)); and X-linked ichthyosis-steroid sulphatase (Jensen et al., *Exp. Cell Res.*, 209:392–397 (1993)).

Alternatively, in the present invention, non-pyrogenic DNA can deliver eukaryotic expression cassettes encoding immunoregulatory molecules. These immuno-regulatory molecules include, but are not limited to, growth factors, such as M-CSF, GM-CSF; and cytokines, such as IL-1, IL-2, IL-4, IL-5, IL-6, IL-10, IL-12, IL-13 TNF-α or IFN-γ (Paul (ed), In: *Fundamental Immunology (Third Eddition)*, Raven Press, NY). Recently, delivery of cytokine expression cassettes to tumor tissue has been shown to stimulate potent systemic immunity and enhanced tumor antigen presentation without producing a systemic cytokine toxicity (Golumbek et al, *Canc. Res.*, 53:5841–5844 (1993); Golumbek et al, *Immun. Res.*, 12:183–192 (1993); Pardoll, *Curr. Opin. Oncol.*, 4:1124–1129 (1992); and Pardoll, *Curr. Opin. Immunol.*, 4:619–623 (1992)).

The antisense RNA and catalytic RNA species delivered to animal cells can be targeted against any molecule present within the recipient cell or likely to be present within the recipient cell. These include but are not limited to RNA species encoding cell regulatory molecules, such as interlukin-6 (Mahieu et al, *Blood*, 84:3758–3765 (1994)), oncogenes such as ras (Kashani-Sabet et al, *Antisen. Res. Devel.*, 2:3–15 (1992)), causitive agents of cancer such as human papillomavirus (Steele et al, *Canc. Res.*, 52:4706–4711 (1992)), enzymes, viral RNA's and pathogen derived RNA's such as HIV-1 (Meyer et al, *Gene*, 129:263–268 (1993); Chatterjee et al, *Sci.*, 258:1485–1488 (1992); and Yamada et al, *Vixol.*, 205:121–126 (1994)). The RNAs can also be targeted at non-transcribed DNA sequences, such as promoter or enhancer regions, or to any other molecule present in the recipient cells, such as but not limited to, enzymes involved in DNA synthesis or tRNA molecules (Scanlon et al, *Proc. Natl. Acad. Sci. USA*, 88:10591 10595 (1991); and Baier et al, *Mol. Immunol.*, 31:923–932 (1994)).

In the present invention, non-pyrogenic DNA can also deliver eukaryotic expression cassettes encoding proteins to animal tissue from which they can later be harvested or purified. An example is the delivery of a eukaryotic expression cassette under the control of a mammary specific viral promoter, such as derived from mouse mammary tumor virus (ATCC No. VR731), encoding $\alpha_1$-antitrypsin to mammary tissue of a goat or sheep.

As a further alternative, single or multiple eukaryotic expression cassettes encoding tumor-specific, transplant, and/or autoimmune antigens, can be delivered in any single or multiple combination with eukaryotic expression cassettes encoding immunoregulatory molecules or other proteins.

The non-pyrogenic DNA containing the eukaryotic expression cassette can also be used to treat animal cells that are cultured in vitro. The animal cells could be further cultured in vitro, and the cells carrying the desired genetic trait can be enriched by selection for or against any selectable marker introduced to the recipient cell at the time of treatment with the DNA partially or completely encapsulated in non-pyrogenic LPS or lipid A. Such markers may include antibiotic resistance genes, e.g., hygromycin, or neomycin, selectable cell surface markers, or any other phenotypic or genotypic element introduced or altered by transfection mediated by non-pyrogenic DNA. These in vitro-treated cells or the in vitro-enriched cells can then be introduced into animals intravenously, intramuscularly, intradermally, or intraperitoneally, or by any inoculation route that allows the cells to enter the host tissue.

Alternatively, the non-pyrogenic DNA containing the eukaryotic expression cassettes can be introduced to infect the animal by intravenous, intramuscular, intradermal, intraperitoneally, intranasal, intra-ocular, intrarectal, intravaginal, oral, immersion and intraurethral inoculation routes.

The amount of the non-pyrogenic DNA of the present invention to be administered will vary depending on the species of the subject, the desired cellular target, route of administration, as well as the disease or condition that is being treated. Generally, the dosage employed will be about 1 ng to 1 g of DNA partially or completely encapsulated in non-pyrogenic LPS/lipid A. Alternatively, when transfecting individual cells in vitro, the dosage of non-pyrogenic DNA administered will vary depending on the cells but generally the dosage employed will be about 1 ng to 1 g of non-pyrogenic DNA.

The non-pyrogenic DNA of the present invention are generally administered along with a pharmaceutically acceptable diluent. The particular pharmaceutically acceptable carrier or diluent employed is not critical to the present invention. Examples of diluents include a PBS, RPNI or DMEM medium; buffer such as citrate buffer (pH 7.0) containing sucrose; bicarbonate buffer (pH 7.0) alone (Levine et al, *J. Clin. Invest.*, 79:888–902 (1987); and Black et al *J. Infect. Dis.*, 155:1260–1265 (1987)), or bicarbonate buffer (pH 7.0) containing ascorbic acid (Levine et al, *Lancet*, II:467–470 (1988)).

3. Preparation of Non-pyrogenic Proteins and Polysaccharides

As another application, non-pyrogenic bacterial strains can be used as a host strain for the expression of proteins and polysaccharides important in biomedical and research applications. The advantage being that the proteins and polysaccharides can be purified by standard procedures without the need for extensive additional processing to remove LPS.

Examples of biomedically important recombinant proteins include but are not restricted to $\alpha$1-antitrypsin, factor X, epidermal growth factor, nerve growth factor, biologically active peptides, calmodulin, erythropoietin, insulin, growth hormone, eostrogen, progesterone, granulocyte/macrophage-colony stimulating factor (GM-CSF), macrophage-colony stimulating factor (M-CSF), interleukins 1, 2, 3, 4, 5, 6, 7, 8, 9, 10, 11, 12, and 13, tumor necrosis factor $\alpha$, interferons $\alpha$, $\beta$, and $\gamma$, and monoclonal antibodies (Nilsen-Hamilton (ed), In: *Growth factors and development*, Current Topics in Developmental Biology vol. 24 (1990); Darnell et al (eds), In: *Molecular Cell Biolocy* (2ed), Scientific American Books, W.H. Freeman & Co. NY (1990), Alberts et al (eds), In: *Molecular biology of the cell*, Garland Publishing Inc., NY (1983); Harlow and Lane (eds), Zn: *Antibodies: A Laboratory Manual*, Cold Spring Harbor, N.Y., pp139–244 (1988); Paul (ed), supra). These and other proteins could be of any mammalian source such a mouse, rat, goat, cattle, sheep, non-human primates, and human.

Purification of the recombinant proteins is accomplished using well-known standard procedures such as size exclusion chromatography, affinity chromatography, anion or cation exchange chromatography, electropheoretic methods, gel electrophoresis, immunoprecipitation, and isoelectrophoretic methods (Harris and Angal (eds), In: *Protein Purification abdications: A practical approach*. IRL Press, Washington D.C. (1986)). Fractions can be dialysed against a suitable diluent such as PBS or normal saline and may be concentrated using precipitation, chromatographic or ultrafiltration techniques (Harris and Angal (eds), supra). Sterility can be obtained by filtration through a 0.1 to 0.45 $\mu$m filter (Millipore). Purity of the non-pyrogenic proteins can be examined using HPLC, SDS-PAGE or silver staining procedures (Hames and Rickwood (eds), In: *Gel electrophoresis of proteins: A practical approach*. IRL Press, Washington D.C. (1981); Harris and Angal (eds), supra). The low pyrogenicity of the protein product is certified in a relavant animal model such as galatosamine-sensitized mice (Galanos et al, supra).

Examples of polysaccharides include but are not restricted to the capsular polysaccharides of Heamophilus spp., Neiseria spp, Klebsiella spp., Staphylococcus spp., Streptococcus spp, and Salmonella spp (Devi et al, *Infect Immun* U63:2906–2911 (1995); Szu et al, *Infect Immun* 62:4440–4444 (1994); de Velasco et al, *Infect Immun* 62:799–808 (1994); Vella and Ellis, *Ped Res* 29:10–13 (1990); Woodrow and Levine (eds), supra and Cryz (ed), supra).

Purification of the bacterial capsular polysaccharides is accomplished using standard procedures such as size exclusion chromatography, affinity chromatography, anion or cation exchange chromatography, electropheoretic methods, gel electrophoresis, immunoprecipitation, and isoelectrophoretic methods (Caplin and Kennedy (eds), In: *Carbohydrate analysis: A practical approach*, IRL Press, Washington D.C. (1986); Devi et al, supra; Szu et al, supra; de Velasco et al, supra; Vella and Ellis, supra; Woodrow and Levine (eds), supra and Cryz (ed), supra); Harlow and Lane (eds), supra pp421–470). Fractions can be dialysed against a suitable diluent such as PBS or normal saline and may be concentrated using precipitation, chromatographic or ultrafiltration techniques (Caplin and Kennedy (eds), supra). Sterility can be obtained by filtration through a 0.1 to 0.45 $\mu$m filter (Millipore). Purity of the non-pyrogenic polysaccharide can be examined using HPLC, SDS-PAGE or silver staining procedures (Chaplin and Kennedy (eds), supra; Sambrook et al (eds), supra).

Alternatively, the polysaccharide could be an O-polysaccharide. Examples of O-polysaccharides of gram negative pathogens include but not restricted to the O-polysaccharides of Salmonella spp, Vibrio cholerae 01 and 0139, Pseudomonas spp., Shigella spp., Campylobacter spp, Neiseria spp., Heamophilus spp., Escherichia spp., Aeromonas spp., Franciesella spp., Corynebacterium spp, Citrobacter spp, Chlamydia Spp., Brucella spp., and Helicobacter spp (Johnson and Perry, *Can J microbiol* 22:29–34 (1976).; Konadu et al, *Infect Immun* 62:5048–5054 (1994); Schiff et al, *Infect Immun* 61:975–980 (1993); Hatano et al, *Infect Immun* 62:3608–3616 (1994); Formal et al, supra; and Cryz (ed), supra). The O-polysaccharides are purifed using the hot water-phenol procedure (Wesphal and Jann, *Meth Carbo Chem* 5:83–91 (1965); Konadu et al, supra). The O-polysacharide can be separated from the core by mild acid hydrolysis (Clarke et al, *Anal Biochem* 199:68–74 (1991)) and purified by extraction with an organic solvent such as ether or chloroform (Clarke et al, supra).

These non-pyrogenic capsular polysaccharides and O-polysacharides can be used as vaccines. To increase the immunogenicity of the bacterial capsular polysaccharides and O-polysacharides in infants, these antigens can be coupled to a protein carrier such as tetanus toxoid (Devi et al, supra; Szu et al, supra; Johnson and Perry, supra; Konadu et al, supra; Formal et al, supra; Schiff et al, supra; Hatano et al, supra and Cryz (ed), supra). The polysaccharide-protein conjugates then are formulated in appropriate commercially available diluents and adjuvants (Johnson and Perry, supra; Konadu et al, supra; Formal et al, supra; Schiff et al, supra; Hatano et al, supra and Cryz (ed), supra). Sterility of the non-pyrogenic polysaccharides can be obtained by filtration through 0.1 $\mu$m filters (Millipore). Purity is examined using immunoblot and silver staining procedures (Hames and Rickwood (eds), supra; Chaplin and Kennedy, supra; Sambrook et al (eds), supra). Safety and potency of the non-pyrogenic vaccines are determined in the appropriate animal models (Johnson and Perry, supra; Konadu et al, supra; Formal et al, supra; Schiff et al, supra; Hatano et al, supra and Cryz (ed), supra) and in Phase 1 volunteer studies (Cryz (ed), supra).

4. Preparation of Non-pyrogenic Vaccines

As a further alternative, the non-pyrogenic bacteria can be given as live attenuated or inactivated vaccine preparations. The advantage of using non-pyrogenic bacterial strains as inactive or live vaccines is the low toxicity and preserved antigenicity of these strains. The particular non-pyrogenic bacteria employed as a vaccine in the present invention is not critical thereto and could be any gram negative bacterium of biomedical or veterinary importance. Examples of such gram-negative bacteria include, but are not limited to, Escherichia spp, Shigella spp, Salmonella spp, Campylobacter spp, Neiseria spp., Haemophilus spp and Rhodobacter spp, Aeromonas spp, Franciesella spp, Corynebacterium spp, Citrobacter spp, Chlamydia spp, Brucella spp, Pseudomonas spp, Helicobacter spp, or Vibrio spp and are described in detail above.

The preparation of such non-pyrogenic bacterial vaccines is accomplished by introducing a one or more mutations in the kdsA, kdsB, kdtA, lpxA, lpxB, lpxC, lpxD, ssc, pmr, htrB, and the msbB genes (Rick et al, supra; Rick and Osborn, supra; Raetz et al, supra; Raetz, supra (1990); Raetz, supra (1993); and Schnaitman and Klena, supra; Lee et al, supra; Karow and Georgopoulos, supra; and Karow et al, supra), either alone or in any combination, which affect the biosynthesis of lipid A and result in the synthesis of non-pyrogenic lipid A structures. Mutations can be introduced into bacterial pathogens are delineated above.

These mutations can be introduced in conjunction with one or more additional mutations. Examples of such additional mutations include, but are not limited to:

(i) auxotrophic mutations, such as aro (Hoiseth et al, *Nature*, 291:238–239 (1981)), qua (McFarland et al, *Microbiol. Path.*, 3:129–141 (1987)), and (Park et al, *J. Bact.*, 170:3725–3730 (1988), thy (Nnalue et al, *Infect. Immun.*, 55:955–962 (1987)), and asd (Curtiss, supra) mutations;

(ii) mutations that inactivate global regulatory functions, such as cya (Curtiss et al, *Infect. Immun.*, 55:3035–3043 (1987)), crp (Curtiss et al (1987), supra), phoP/phoQ (Groisman et al, *Proc. Natl. Acad. Sci., USA*, 86:7077–7081 (1989); and Miller et al, *Proc. Natl. Acad. Sci., USA*, 86:5054–5058 (1989)), phoP$^c$ (Miller et al, *J. Bact.*, 172:2485–2490 (1990)) or ompR (Dorman et al, *Infect. Immun.*, 57:2136–2140 (1989)) mutations;

(iii) mutations that modify the stress response, such as recA (Buchmeier et al, *Mol. Micro.*, 7:933–936 (1993)), htrA (Johnson et al, *Mol. Micro.*, 5:401–407 (1991)), htpR (Neidhardt et al, *Biochem. Biophys. Res. Com.*, 100:894–900 (1981)), hsp (Neidhardt et al, *Ann. Rev. Genet.*, 18:295–329 (1984)) and groEL (Buchmeier et al, *Sci.*, 248:730–732 (1990)) mutations;

(iv) mutations in specific virulence factors, such as lsyA (Libby et al, *Proc. Natl. Acad. Sci., USA*, 91:489–493 (1994)), pag or pro (Miller et al (1990), supra; and Miller et al (1989), supra), iscA or virG (d'Hauteville et al, *Mol. Micro.*, 6:833–841 (1992)), picA (Mengaud et al, *Mol. Microbiol.*, 5:367–72 (1991); Camilli et al, *J. Exp. Med, Med*, 173:751–754 (1991)), and act (Brundage et al, Proc. *Natl. Acad. Sci., USA*, 90:11890–11894 (1993)) mutations;

(V) mutations that affect DNA topology, such as topA (Galan et al, *Infect Immun.* 58:1879–1885 (1990)) mutation;

(vi) mutations that alter the biogenesis of surface polysaccharides, such as rfb, galE (Hone et al, *J. Infect.*

Dis., 156:164–167 (1987)) or via (Popoff et al, *J. Gen. Microbiol.*, 138:297–304 (1992)) mutations;

(vii) mutations that modify suicide systems, such as sacB (Recorbet et al, *App. Environ. Micro.*, 59:1361–1366 (1993); Quandt et al, *Gene*, 17o:15–21 (1993)), nuc (Ahrenholtz et al, *App. Environ. Micro.*, 60:3746–3751 (1994)), hok, gef, kil, or phiA (Molin et al, *Ann. Rev. Microbiol.*, 47:139–166 (1993)) mutations;

(viii) mutations that introduce suicide systems, such as lysogens encoded by P22 (Rennell et al, *Virol.*, 143:280–289 (1985)), λ murein transglycosylase (Bienkowska-Szewczyk et al, *Mol. Gen. Genet.*, 184:111–114 (1981)) or S-gene (Reader et al, *Virol.*, 43:623–628 (1971)); and (ix) mutations that disrupt or modify the correct cell cycle, such as minC (de Boer et al, *Cell*, 56:641–649 (1989)) mutation.

The mutations can be either constitutively expressed or under the control of inducible promoters, such as the temperature sensitive heat shock family of promoters (Neidhardt et al, supra), or the anaerobically induced nirB promoter (Harborne et al, *Mol. Micro.*, 6:2805–2813 (1992)) or repressible promoters, such as uapA (Gorfinkiel et al, *J. Biol. Chem.*, 268:23376–23381 (1993)) or gcv (Stauffer et al, *J. Bact.*, 176:6159 6164 (1994)).

As an additional advantage non-pyrogenic bacterial vaccines induce Type 2 T helper cells. The immune response is regulated by two major classes of T helper cells called Type 1 (Th1) and Type 2 (Th2). Th1 predominantly produce IL-2 and IFN-γ, whereas Th2 predominantly produce IL-2 and IL-4/5 (Paul (ed), supra). When Th1 cells predominate IgG2b is the main antibody isotype in the serum IgG response by mice, whereas when Th2 cells predominate IgG1 is the main antibody isotype in the serum IgG response in mice (Paul (ed), supra). Since endotoxin drives the host immune response in the direction of Th1 predominance (Mattern et al *J Immunol* 153:2996–3004 (1994); Fruh et al, *Infect Immun* 63:1107–1112 (1995)), the absence of endotoxin activity in htrB mutants results in induction of Th2 cells and strong IgG1 and mucosal secretory IgA responses (Pascual et al, *Immuno Meth* 5:56–72 (1994)).

Bacterial vaccines where the induction of Th2 cells and mucosal secretory IgA responses is beneficial include, but are not limited to, Mycobacterium spp., *Helicobacter pylori*, Salmonella spp., Shigella spp., Campylobacter spp, *E. coli*, Listeria spp., *Legionella pneumoniae*, Pseudomonas spp., and Vibrio spp., vaccines (Woodrow and Levine (eds), supra; Cryz (ed), supra; and Wachsmuth et al (eds), supra)

The non-pyrogenic vaccines are cultured as described above and prepared under GLP or GMP conditions as described (In: *US Code of Federal Regulation* 210–211, *Good Manufacturing Practices*, Food and Drug Administration, CBER, Rockville Md.). Safety and potency of the non-pyrogenic vaccines are determined in the apropriate animal models (In: *US Code of Federal Regulation* 314.126, *Adeauate and well-controled trials*, CBER, Rockville Md.)) and in Phase 1 volunteer studies (In: *US Code of Federal Regulation* 50, *Protection of human subjects*, Food and Drug Administration, CBER, Rockville Md.). The non-pyrogenic vaccines can be given as inactivated preparations by the parenteral route or as live or inactivated preparations by the intranasal, oral or vaginal routes or combinations thereof (Woodrow and Levine (eds), supra; Cryz (ed), supra; and Wachsmuth et al (eds), supra).

The particular pharmaceutically acceptable carrier or diluent employed is not critical to the present invention. Examples of diluents include a phosphate buffered saline; normal saline; RPMI or DMEM medium; buffer for buffering against gastric acid in the stomach; such as citrate buffer (pH 7.0) containing sucrose; bicarbonate buffer (pH 7.0) alone (Levine et al, *J. Clin. Invest.*, 79:888–902 (1987); and Black et al *J. Infect. Dis.*, 155:1260–1265 (1987)), or bicarbonate buffer (pH 7.0) containing ascorbic acid, lactose, and optionally aspartame (Levine et al, *Lancet*, II:467–470 (1988)). Examples of carriers include proteins, e.g., as found in skim milk, sugars, e.g., sucrose, or polyvinylpyrrolidone. Typically these carriers would be used at a concentration of about 0.1–90% (w/v) but preferably at a range of 1–10% (w/v).

5. Preparation of Non-pyrogenic Vaccine Vectors

As a further alternative, said non-pyrogenic bacteria can be given as live attenuated or inactivated vaccine vectors that deliver protective antigens cloned from other pathogens (see below). The particular non-pyrogenic bacteria employed as a vaccine vector in the present invention is not critical thereto and could be any gram negative bacterium. Examples of such gram-negative bacteria include, but are not limited to, Escherichia spp, Shigella spp, Salmonella spp, Neiseria spp, Haemophilus spp, Campylobacter spp, Aeromonas spp, Franciesella spp, Corynebacterium spp, Citrobacter spp, Chlamydia spp, Brucella spp, Pseudomonas spp, Helicobacter spp, or Vibrio spp and are described in detail above.

As used herein the expression of "protective antigens" means antigens or epitopes thereof which give rise to protective immunity against infection by the pathogen from which they are derived. The protective antigen may be a polysaccharide, protein or antigenic fragment thereof from viral pathogens, bacterial pathogens, and parasitic pathogens. Alternatively, the vaccine antigen may be a synthetic gene, constructed using recombinant DNA methods, which encode antigens or parts thereof from viral, bacterial, parasitic pathogens. These pathogens can be infectious in humans, domestic animals or wild animal hosts.

The antigen can be any molecule that is expressed by any viral, bacterial, parasitic pathogen prior to or during entry into, colonization of, or replication in their animal host or their invertebrate vectors. Multiple antigens can be delivered by the non-pyrogenic bacterial vaccine vectors that induce immune responses against any combination of viral, bacterial, parasitic antigens, or synthetic genes encoding all or parts or any combination of viral, bacterial, parasitic antigens.

The viral pathogens, from which the viral antigens are derived, include, but are not limited to, Orthomyxoviruses, such as influenza virus; Retroviruses, such as RSV and SIV, Herpesviruses, such as EBV; CMV or herpes simplex virus; Lentiviruses, such as human immunodeficiency virus; Rhabdoviruses, such as rabies; Picornoviruses, such as Poliovirus; Poxviruses, such as vaccinia; Rotavirus; Papalomavirus; and Parvoviruses. Examples of specific antigens of the viral pathogens, which are delivered by the non-pyrogenic vaccine vector, are described above.

The bacterial pathogens, from which the bacterial antigens are derived, include but are not limited to, Mycobacterium spp., *Helicobacter pylori*, Salmonella spp., Shigella spp., *E. coli*, Rickettsia spp., Listeria spp., *Legionella pneumoniae*, Pseudomonas spp., Vibrio spp., and *Borellia burgdorferi*. Examples of specific antigens of the bacterial pathogens, which are delivered by the non-pyrogenic vaccine vector, are described above.

The parasitic pathogens, from which the parasitic antigens are derived, include but are not limited to, Plasmodium spp., Trypanosome spp., Giardia spp., Boophilus spp., Babesia spp., Entamoeba spp., Eimeria spp., Leishmania spp., Schistosome spp., Brugia spp., Fascida spp., Dirofilaria spp., Wuchereria spp., and Onchocerea spp. Examples of specific antigens of the parasitic pathogens, which are delivered by the non-pyrogenic vaccine vector, are described above.

In the present invention, the non-pyrogenic bacterial vaccine vector can also deliver antigens encoding a therapeutic agent. For example, the expression cassettes can encode tumor-specific, transplant, or autoimmune antigens or parts thereof. Alternatively, the expression cassettes can encode synthetic genes, which encode tumor-specific, transplant, or autoimmune antigens or parts thereof.

As discussed above an additional advantage over improved safety, non-pyrogenic bacterial vaccine vectors induce Th2 responses and strong mucosal secretory IgA responses. A vaccine vector that induces predominantly Th2 cells will be useful when targetting the immune response against pathogens that are limited or prevented by mucosal secretory IgA responses (Pascual et al, supra). There are numerous examples of viral, parasitic, and bacterial vaccines where mucosal secretory IgA immunity is preferred (Pascual et al, supra; Woodrow and Levine (eds), and supra; Cryz (ed), supra).

Example of bacterial pathogens where induction of Th2 responses and the induction of mucosal secretory IgA against said pathogen would be beneficial include, but are not limited to, Mycobacterium spp., *Helicobacter pylori*, Salmonella spp., Campylobacter spp., Shigella spp., *E. coli*, Listeria spp., *Legionella pneumoniae*, Pseudomonas spp., and Vibrio spp. Specific examples of protective antigens of bacterial pathogens are described above.

Example of viral pathogens where induction of Th2 responses and the induction of mucosal secretory IgA against said pathogens would be beneficial include, but are not limited to, Orthomyxoviruses, such as influenza virus; Retroviruses, such as RSV and SIV; DNA viruses such as Hepatitis A and B; Herpesviruses, such as EBV, CMV or herpes simplex virus; Lentiviruses, such as human immunodeficiency virus; Rhabdoviruses, such as rabies; Picornoviruses, such as poliovirus; Rotavirus; and Parvoviruses. Specific examples of protective antigens of viral pathogens are described above.

Example of parasitic pathogens where induction of Th2 responses and the induction of mucosal secretory IgA against said pathogens would be beneficial include, but are not limited to, Giardia spp., Entamoeba spp., and Schistosome spp. Specific examples of protective antigens of parasitic pathogens are described above.

Non-pyrogenic bacterial vaccine vectors can also be employed to introduce endogenous or foreign eukaryotic expression cassettes into animal cells or tissue (U.S. patent pending Ser. No. 08/433,790 (1995)). The method allows for the delivery of eukaryotic expression cassettes encoding the endogenous or foreign genes into animal cells or animal tissue, and is useful for expressing, e.g., vaccine antigens, therapeutic agents, immunoregulatory agents, antisense RNAS, and catalytic RNAs, in animal cells or animal tissue (U.S. patent pending Ser. No. 08/433,790 (1995)).

The non-pyrogenic bacterial vaccine vectors are cultured as described above and prepared under GMP conditions as described (In: *US Code of Federal Regulation* 210–211, *Good Manufacturing Practices*, Food and Drug Administration, CBER, Rockville Md.). Safety and potency of the non-pyrogenic vaccine vectors are determined in the apropriate animal models (In: *US Code of Federal Regulation* 314.126, *Adecuate and well-controled trials*, CBER, Rockville Md.)) and in Phase 1 volunteer studies (In: *US Code of Federal Regulation* 50, *Protection of human subjects*, Food and Drug Administration, CBER, Rockville Md.). The non-pyrogenic bacterial vaccine vectors can be given as inactivated preparations by the intranasal, oral or parenteral routes or as live preparations by the intranasal, oral or vaginal routes or combinations thereof (Woodrow and Levine (eds), supra; Cryz (ed), supra; and Wachsmuth et al (eds), supra).

These vaccine vectors are generally administered along with a pharmaceutically acceptable carrier or diluent as delineated above.

The following examples are included to demonstrate the preferred embodiments of the invention but are not intended to be limiting:

EXAMPLE 1

Production of Bacteria That Poorly Activate TNFα Secretion by Peripheral Blood Mononuclear Cells Mutant strain MLK53 of *E. coli* containing a transposon Tn10 insertion in the htrB locus was obtained from Dr. Margaret Karow (Karow and Georgopoulos, supra). The basis for the temperature-sensitive growth phenotype of the htrB mutant has remained criptic (Karow and Geogopoulos, supra). There has been speculation that these mutants produce defective lipid A precursors (Karow and Geogopoulos, supra). This was based on the observation that quaternary cationic compounds enabled these mutants to grow in non-permissive temperatures (Lee et al, supra). Their hypothesis was that the quaternary cationic compounds influenced the intermolecular interation between LPS molecules in the outer membrane. However, they did not provide any direct evidence that their htrB mutants produce substantially pure non-pyrogenic LPS. More importantly, these investigators did not show that these mutants would have the surprisingly broad biotechnology applications as described herein.

We postulated that growth of htrB mutants under non-permissive conditions in the presence of quaternary cationic compounds should result in the production of bacteria that contains substantially pure non-toxic LPS. Therefore, we determined whether growth of the htrB mutants in TTAB under non-permissive conditions results in the production of non-pyrogenic LPS. To identify non-permissive growth conditions, Luria-Bertani (herein LB) broth (Miller (ed), In: *A Short Course in Bacterial Genetics*, Cold Spring Harbor Press, N.Y. (1992)) is supplemented with TTAB at a final concentration 0 and 0.5 to 64 $\mu$g/ml in 2-fold serial steps. These cultures are inoculated at a starting density of about $10^6$ cfu/ml with *E. coli* htrB mutant MLK53 (Lee et al, supra). The strains are cultured at 30° C. (permissive) or 37° C. and 42° C. (non-permissive) with shaking (200 opm) for 16 hours. Strain MLK53 grows 37° C. and 42° C. in LB supplemented with TTAB ranging from 4 to 16 $\mu$g/ml. The most rapid growth for MLK53 37° C. and 42° C. occurs in LB supplemented with TTAB at 8 $\mu$g/ml.

There are several assays that measure endotoxin activity. These include polyclonal B lymphocyte proliferation, peripheral blood mononuclear cells (PBMC) activation, and the galactosamine-sensitized mouse, assays (Raetz, supra; Rietschel et al, supra). Activation of pro inflammatory cytokine TNFα secretion by human PBMCs is a sensitive assay for endotoxin activity (Raetz, supra; Rietschel et al, supra). Therefore, one measure of pyrogenicity is obtained by measuring the PBMC-activating properties of said non-pyrogenic bacteria compared to wild type *E. coli*. Such an assay provides information on the pyrogenicity of said non-pyrogenic bacterial strains when grown under non-permissive growth conditions. As an example this can be accomplished by comparing the PBMC-activating properties of DH5A to those of htrB mutant MLK53.

Human PBMCs are isolated from whole blood using Lyphocyte Separation Medium$^R$, following the procedure provided by the manufacturer (Organon Teknika Co., Durhan N.C.). These cells are washed twice with RPMI medium (Life Technologies, Gaitesburg Md.) and resuspended in RPMI at a cell density of $6 \times 10^6$ PBMCs/ml.

Strains *E. coli* DH5α and MLK53 are cultured in LB agar supplemented with TTAB (8 μg/ml) at 37° C. for 16 hours. Several single colonies from these plates are transferred to LB broth so that the starting optical density at 600 nm is 0.05 relative to a sterile LB broth control. These LB broth suspensions are cultured at the same temperature for 4 hours with shaking. The cells are harvested by centrifugation at 5000×g and washed in PBS. Control strain DH5α is a commercially-available host strain widely used for many biotechnology applications (Life Technologies, Gaithesburg Md.).

Aliquots of the bacterial suspensions containing $10^3$ colony forming units (cfu) of the DH5α or MLK53 bacilli are added to triplicate wells of a 96 well microtiter plate. Then, $6 \times 10^5$ PBMCs are added to these wells. Control wells contain only PBMCs (negative control) or PBMCs with 10 ng/ml purified *E. coli* LPS (Sigma, St Louis Mo.) (positive control). Culture supernatants are collected after 8 hours incubation at 37° C. in 5% $CO_2$ and TNFA levels are measured by TNFα-specific quantitative ELISA (Pharminogen). An example ELISA shows that MLK53 induced 434±55 pg of TNFα/$10^6$ PBMC. In contrast, DH5α induced >2000 pg of TNFα/$10^6$ PBMC, which is similar to the level of TNFα induced by the LPS control.

The results show that MLK53 bacilli induced significantly less TNFα than DHSα bacilli. The residual activation of PBMCs by MLK53 probably is due to complement-mediated phagocytosis of the bacteria and the shedding of bacterial porins into the culture wells during the 8 hour incubation period. Both these phenomena have been shown to activate PBMCs (Lewis and McGee (eds) In: *The macrophaae: the natural immune system*. IRL press NY pp77–114 (1992); Zwilling and Eisenstein (eds), In: *Macrophage-pathogen interactions*. Marcel Dekker Inc., NY pp29–179 (1994)).

To investigate whether the low PBMC-activating properties of MLK53 relates to the production of non-pyrogenic LPS, LPS is extracted from the htrB::Tn10 mutant strain MLK53 and isogenic htrB$^+$ parent strains W3110 (Karow and Geogopoulos, supra). These strains are cultured in LB agar supplemented with TTAB (8 μg/ml) at 30° C., 37° C., or 42° C. for 16 hours. Several single colonies from these plates are transferred to LB broth so that the starting optical density at 600 nm is 0.05 relative to a sterile LB broth control. These LB broth suspensions are cultured at the same temperatures for 4 hours with shaking until the optical density is 0.8 relative to a sterile LB broth control. LPS is islolated by hot water-phenol extraction procedure (Wesphal and Jann, supra) and lyophilized. The LPS is resuspended in endotoxin-free PBS at a concentration of 10 mg/ml.

Human PBMCs are isolated from whole blood as above using Lyphocyte Separation Medium$^R$ following the manufacturer's instructions (organon Teknika). These cells are washed twice with RPMI medium (Life Technologies, Gaitesburg Md.) and resuspended in RPMI at a density of $6 \times 10^6$ PBMCs/ml.

LPS (18 ng to 180 ng) is added to 96 well microtiter plates. Then, $6 \times 10^5$ PBMCs are added to these wells. Control wells contain only PBMCs (negative control). Culture supernatants were collected after 8 hours incubation at 37° C. in 5% $CO_2$ and TNFα levels are measured by TNFα-specific quantitative ELISA using commercially available assay kits (Pharminogen).

TABLE 1

| | pg TNFα/$10^6$PBMCs in wells with LPS (ng/ml) | | |
|---|---|---|---|
| STRAIN | 180 ng | 60 ng | 18 ng |
| W3110(30° C.) | >2000 | >2000 | >2000 |
| W3110(37° C.) | >2000 | >2000 | >2000 |
| W3110(42° C.) | >2000 | >2000 | >2000 |
| MLK53(30° C.) | 299 ± 34 | 315 ± 57 | 274 ± 63 |
| MLK53(37° C.) | <12 | <12 | <12 |
| MLK53(42° C.) | <12 | <12 | <12 |

Data from a representative experiment (Table 1) shows that LPS isolated from the htrB mutant, MLK53, at non-permissive conditions (37° C. and 42° C.) is non-pyrogenic does not induce detectable levels of the pro-inflammatory cytokine TNFα. In contrast, LPS isolated from wild type strain W3110 under all three growth conditions induces high levels of TNFα.

EXAMPLE 2

Toxicity Assays in Animals

To investigate whether the low PBMC-activating properties of MLK53 LPS also results in low pyrogenicity in animal, a standard well-known LPS toxicity assay is performed in groups of 5 C75B1/6 female mice, which are 4–6 weeks old (Galanos et al, supra; Charles River Co.).

First, LPS is isolated from these strains after culturing in permissive or non-permissive conditions as outlined in example 1 above. To assay the endotoxin properties of this LPS C57B1/6 mice are given intravenously 0.1 ml of endotoxin-free PBS (Sigma) containing LPS (doses ranging from 1 pg to 100 ng in 10-fold serial doses) mixed with galactosamine (300 mg/kg)(Sigma, St Louis Mo.) (Galanos et al, supra). The results are expressed as an $LD_{50}$ value (Welkos and O'Brien, *Meth Enzymol* 235:29–39 (1994)) in ng and show that LPS isolated from the htxB mutant, MLK53, at non-permissive conditions (37° C. and 42° C.) is significantly less toxic for mice that wild type W3110 LPS.

EXAMPLE 3

Immunogenicity of Non-pyrogenic LPS

To evaluate the vaccine potential of the non-pyrogenic LPS purified MLK53 LPS (either alone or conjugated to a carrier protein) is suspended in Fruend's Incomplete Adjuvant (herein FIA) and injected intramuscularly into CD-1 mice (Harlow and Lane, supra pp55–137). The LPS is purified by hot-water phenol extraction (Wesphal and Jann, supra) from MLK53 grown at 37° C. as outlined in example 1 above. The LPS is suspended in normal saline (0.85% w/v NaCl) at 2, 0.2, and 0.02 mg/ml and emulsified with an equal volume of FIA (Harlow and Lane, supra pp55–137). Individual female C57BL/6 mice aged 4–6 weeks (Charles River), in three groups of 5 mice, are then injected subcutaneously with 0.1 ml of these mixtures so that the mice in each group receive 100, 10, and 1 µg of LPS, respectively (Harlow and Lane, supra pp55–137). These groups of mice are boosted with the same dose of LPS 30 days after the primary immunization. The mice are bled from the tail vien before and 15, 30, 45, and 60 days after immunization. Anti-LPS serum IgM and IgG antibody levels in individual mice are quantitated by a standard ELISA (Coligan et al (eds), In: Current Protocols in Immunology, John Wiley and Sons, NY, pp2.1.1–2.1.22 (1991); Harlow and Lane (eds), supra pp553–614).

Alternatively, LPS can be coupled to a carrier protein, so that the immune response becomes T-dependent (Johnson and Perry, supra; Konadu et al, supra; Formal et al, supra; Schiff et al, supra; Hatano et al, supra and Cryz (ed), supra). Coupling is acomplished by standard well-known procedures (Devi et al, supra; Szu et al, supra; de Velasco et al, supra; Vella and Ellis, supra; Johnson and Perry, supra; Konadu et al, supra; Formal et al, supra; Schiff et al, supra; Hatano et al, supra and Cryz (ed), supra). For example LPS can be coupled to formalin-inactivated tetanus toxoid (TT) (Sigma, St Louis MO) by chemical or UV coupling techniques (Devi et al, supra; Szu et al, supra; de Velasco et al, supra; Vella and Ellis, supra; Johnson and Perry, supra; Konadu et al, supra; Formal et al, supra; Schiff et al, supra; Hatano et al, supra and Cryz (ed), supra). The ratio of LPS:TT is varied from 10:1 to 1:1. LPS:TT conjugates are purified by HPLC and examined by SDS-PAGE (Harris and Angal, supra). These preparations are used to immunize mice. The LPS:TT conjugates are suspended in endotoxin-free PBS (Sigma) at 2 mg/ml and emulsified with an equal volume of FIA. Individual mice, in three groups of 5 mice, are then injected with 0.1 ml of these mixtures so that the individual mice in each group receive 100 µg of LPS:TT conjugate (Harlow and Land (eds), supra pp53–137). The mice are boosted,with the same dose of LPS:TT on day 30. The mice are bled from the tail vien before and 15, 30, 45, and 60 days after immunization. Anti-LPS serum IgM and IgG antibody levels in individual mice are quantitated by ELISA (Coligan et al (eds), supra pp2.1.1–2.1.22; Harlow and Lane (eds), supra pp553–614).

This experiment identifies the optimum conjugation ratio for LPS:TT and shows that conjugation changes the response from T-independent (non-boostable) to T-dependent (boostable).

EXAMPLE 4

Purification of Non-pyrogenic DNA

We were interested in the use of lipid A-defective strains for the preparation of non-pyrogenic plasmid DNA and use of the same for introducing endogenous or foreign genes into animal cells or animal tissue. To address this question, we investigated whether plasmid DNA from MLK53 grown under non-permissive growth conditions activated TNFα secretion by PBMCs compared to plasmid DNA from standard host strain DH5α (Life Technologies).

Human PBMCs were isolated, as above. These cells were washed twice with RPMI medium (Life Technologies, Gaitesburg Md.) and resuspended in RPMI at a cell density of ~5×10$^6$ PBMCs/ml.

The recombinant plasmid pSV-βgal (Promega) is introduced into DH5α and MLK53 by electroporation using a Gene Pulser set at 200Ω, 25µF and 2.5 kV (BioRad Laboratories, Hercules, Calif.) as described by the manufacturer (BioRad). Selection for transformants was achieved by growth on LB agar supplemented with ampicillin (100 µg/ml; Sigma) and TTAB (8 µg /ml) at 37° C. for 16 hours.

Plasmid DNA is prepared from strains DH5α carrying pSV-βgal or MLK53 carrying pSV-βgal. Both strains are streaked onto LB-agar containing 8 µg/ml TTAB and grown at 30° C., 37° C., or 42° C. for 16 hours. Several single colonies from these plate-grown bacterial cultures are transferred to LB-broth containing 8 µg/ml TTAB so that the starting optical density at 600 nm is 0.05 relative to a sterile control. These liquid cultures are incubated at 37° C. with shaking until the optical density at 600 nm becomes 0.8 relative to a sterile control. The bacteria are harvested by centrifugation (5000×g) and suspended in 5 ml alkaline-lysis solution 1 (Sambrook et al (eds), supra) at a density of $10^{10}$ cfu/ml. Plasmid DNA is prepared from these cell suspensions by the well-known alkaline lysis method as described (Sambrook et al (eds), supra). After preparing the DNA it is resuspended in endotoxin-free PBS at a concentration of 1 mg/ml.

Aliquots (10 µl) of plasmid pSV-βgal DNA suspended in endotoxin-free PBS (Sigma) containing 1 to 30 µg of DNA (in 3-fold serial dilutions) from strain DH5α or MLK53 were added to triplicate wells of a 96 well microtiter plate. Then 5×10$^5$ PBMCs were added to these wells. Control wells contained only PBMCs (negative control) or PBMCs with 10 ng/ml purified E. coli LPS (Sigma, St Louis Mo.) (positive control). Culture supernatants were collected after 8 hours incubation at 37° C. in 5% $CO_2$ and TNFα levels were measured by TNFα-specific quantitative ELISA (Pharminogen).

The results, shown in Table 2, indicated that the relatively crude plasmid DNA from H808 induced negligible levels of TNFα/10$^6$ PBMC. In contrast, DNA from H799 induced high levels of TNFα/10$^6$ PBMC that were similar to the level of TNFα induced by the LPS control (ie. 10 ng of LPS induces >2000 pg of TNFα/10$^6$ PBMCs).

TABLE 2

| | pg TNFα/10$^6$ PBMCs in wells with plasmid DNA | | |
|---|---|---|---|
| SOURCE OF DNA | 3 µg | 1 µg | 10 ng |
| DH5α(pSV-βgal) | >2000 | >2000 | Not Tested |
| MLK53(pSV-βgal) | 27 ± 6 | <12 | Not Tested |

The remaining activating effect is probably due to the crude preparative technique used to prepare the DNA. It is likely that preparation of DNA from lipid A-defective strains using endotoxin free tubes and DNA-extraction solutions in an endotoxin free GMP laboratory would be virtually free of PMBC-activating endotoxin.

EXAMPLE 5

Transfection and Genetic Immunization with Non-pyrogenic DNA

The recombinant plasmid pSV-βgal (Promega) is introduced into E. coli strains W3110 and MLK53 by electroporation using a Gene Pulser set at 200Ω, 25 µF and 2.5 kV (BioRad Laboratories, Hercules, Calif.) as described by the manufacturer (BioRad). Selection for transformants is achieved by growth on LB agar supplemented with ampicillin (100 µg/ml; Sigma) and TTAB (8 µ/ml) at 37° C. for 16 hours. Plasmid DNA is prepared from strains W3110 (pSV-βgal) or MLK53(pSV-βgal), which were cultured on LB agar then in LB broth supplemented with TTAB at 37°

C. as outlined above in example 1. Plasmid DNA is purified by the standard alkaling lysis method as described (Sambrook et al (eds), supra) and suspended in PBS at a concentration of 1 mg/ml. The DNA is encapsulated in Lipofectamine$^R$ by the manufacturer's procedure (Life Technologies Inc., Gaithesburg Md.).

HeLa cells (ATCC-CCL2) are grown at 37° C./5% (v/v) $CO_2$ in RPMI 1640 medium (Life Technologies) supplemented with 1 mM pyruvate, 10% heat-inactivated bovine serum,50 U/ml penicillin, and 50 µg/ml streptomycin (Life Technologies). These cells are plated into 48-well culture plate at a density of 5×10$^5$ cells/well. The cells are treated with 50 to 0.1 µg of DNA encapsulated in Lipofectamine$^R$ (Life Technologies). The cells are washed 3 hours after treatment and incubated for 48 hours at 37° C. in 5% v/v $CO_2$. The level of β-galactosidase in each well is quantitated as described (Rosenthal et al, *Meth Enzymol* 152:704–721 (1987); Promega Technical Bulletin TB097 (1993)).

This experiment shows that pSV-βgal DNA from strain MLK53 is as effective as pSV-βgal DNA from W3110 at transfecting HeLa cells to β-galacosidase-positive phenotype.

Plasmid DNA can also be used to immunize animals (Robinson et al, supra; Ulmer et al, supra). Thus, the non-pyrogenic pSV-βgal DNA isolated from strain MLK53 can be used to immunize mice. Procedures for genetic immunization of mice has been described (Robinson et al, supra; Ulmer et al, supra). 50 µl PBS containing 100 µg of pSV-βgal DNA isolated from non-pyrogenic strain MLK53 is injected intramuscularly into a group of five C57BL/6 mice. It is optimal to use 6–8 week old female C57BL/6 mice (weight 19–21 µm). Mice should be anaesthetized with sodium pentobarbital (75 mg/kg IP) since awake mice will contract their muscles and squeeze the DNA solution out. After the mice are asleep, the hindlimbs are shaved to better reveal the tibial bone and the access to the tibialis anterior (TA) muscle (Popesko et al (eds), In: *A colour atlas of anatomy of small laboratory animals* vol. 2, Wolfe Publishing, London England (1992)). Shaving of the limbs allows much greater precision and thus reproducibility for the actual injection step. In preparation for the intramuscular injection, DNA is dissolved in endotoxin-free injectable PBS and is best at 2 mg/ml. Each TA muscle is injected with 50 µl of DNA solution. To inject plasmid DNA use a 27GX3/4" (0.4×20 mm) needle attached to a 1 ml tuberculin syringe. A piece of polyethylene tubing (PE 20, ID=0.38 mm) should be fit over the needle such that only 2–3 mm of needle protrudes (basically just the beveled portion should protrude). Fill the syringe with the DNA solution, attach the needle and then slowly fill the needle so that no air bubbles are trapped. The problem of dead volume is simplified using an insulin syringe. Inject through the skin—the tip of the needle should be about 3 mm lateral to the anterior tibial tuberosity (this is about half way between the knee and the ankle), keeping the needle almost perpendicular to the tibia. Once the needle is in place (push in until the end of the PE tubing rests against the skin with a bit of pressure), inject the 50 µl DNA solution slowly (over approximately 10 sec), hold the needle in place for another 5–10 sec, then remove the needle slowly. If the needle is accidentally pulled out before injection, try to reinsert it in the same hole, otherwise leakage is experienced (It is a good idea to practice injections with Indian ink or some other colored substance to make sure the injection is placed in the TA and only the TA—a good injection will not color any muscles other then the TA).

Serum is collected before and on days 28 and 44 after immunization. About 400–500 µl of blood is collected into individual microfuge tubes from the tail vein of each mouse and allowed to clot by incubating for 16 hrs at 4° C. After centrifugation in a microfuge for 5 min, the sera samples are transferred to fresh tubes and stored at −20° C. Serum IgG against bacterial β-galactosidase is measured by ELISA (Coligan et al (eds), supra pp2.1.1–2.1.22; Harlow and Lane (eds), supra pp553–614).

This experiment shows that non-pyrogenic pSV-βgal DNA from strain MLK53 elicits an immune response against β-galactosidase.

EXAMPLE 6

Extraction and Activity of Non-pyrogenic Recombinant Protein

Non-pyrogenic bacteria are capable of producing non-pyrogenic recombinant proteins that retained their biological activity. Thus, for example the said non-pyrogenic bacterial strains can be used to produce IL-10 (Howard et al, *J Clin Immunol* 12:239–247 (1991); Vieira et al, *Proc Natl Acad Sci* 88:172–176 (1991)). Sequences encoding IL-10 (GenBank Accession number M37897; Moore et al, *Science* 248:1230–1234 (1990)) are amplified by polymerase chain reaction (herein PCR) (Innis et al (eds), In: *PCR protcols: A guide to methods and applications*. Academic Press Inc., NY (1990)) using primers specific for the 5' (5'-ATGCCTGGCTCAGCACTG) (SEQ ID NO:1) and 3' (5'-TTTAGCTTTTCATTTTGATC) (SEQ ID NO:2) ends of the IL-10-encoding sequences from plasmid pcD(SRα)-F115 (Moore et al, supra). These PCR generated IL-10-encoding sequences are introduced into a commercially available expression vector such as pBluescipts (Stratagene) resulting in plasmid pIL-10. Plasmid pIL10, which expresses IL-10 in *E. coli*, is introduced into non-pyrogenic strain *E. coil* MLK53 or control strain *E. coli* W3110 using standard bacterial transformation proceudures (Sambrook et al (eds), supra). Crude preparations of IL-10 are extracted as described (Howard et al, supra; Vieira et al, supra). In brief, strains MLK53(pIL10) and W3110(pIL10) are streaked onto LB-agar containing 8 µg/ml TTAB and grown at 37° C. for 16 hours. Several single colonies from these plate-grown bacterial cultures are transferred to LB-broth containing 8 µg/ml TTAB so that the starting optical density at 600 nm is 0.05 relative to a sterile control. These liquid cultures are incubated at 37° C. with shaking until the optical density at 600 nm becomes 0.8 relative to a sterile control. The bacteria are harvested by centrifugation and resuspended in PBS at a density of 10$^{10}$ cfu/ml. These bacterial suspensions are sonicated on ice for 5 minutes in 30 second bursts. The cell debris and unlysed cells are removed by centrifugation at 45,000 g (Howard et al, supra; Vieira et al, supra). The supernatants containing IL-10 and the control supernatants are collected and filter-sterilized through a 0.45 µM filter (Millipore).

The level of IL-10 activity present in these preparations is quantitated by dose-dependent co-stimulation of MC/9 cells with murine IL-4 (Thompson-Snipes et al, *J Exp Med* 173:507–510 (1991)).

To assay the endotoxin activity of MLK53 (pIL10) supernatants versus the W3110(pIL10) supernatant, aliquots of each supernatant in 2-fold serial dilutions from strain MLK53(pIL10) and W3110(pIL10) are added to triplicate wells of a 96 well microtiter plate. Then, 5×10$^5$ PBMCs are added to these wells. Control wells contained only PBMCs (negative control) or PBMCs with 10 ng/ml purified *E. coli* LPS (Sigma, St Louis Mo.) (positive control). Culture supernatants are collected after 8 hours incubation at 37° C. in 5% $CO_2$ and TNFα levels are measured by TNFα-specific quantitative ELISA (Pharminogen).

The results show that the htrB mutant MLK53 is a useful host for the production of non-pyrogenic cloned recombinant cytokines such as IL-10.

EXAMPLE 7

Immunogenicity of a Non-pyrogenic Protein

To produce a non-pyrogenic recombinant protein which retains immunogenic activity, we introduced pTRF2 (Fouts et al, *Vaccine* 13:561–569 (1q95)) into MLK53 or W3110 using standard transformation procedures (Sambrook et al (eds), supra). This plasmid expresses recombinant gp120 (rgp120) in the cytoplasm of the host bacterial strains (Fouts et al, supra). Crude preparations of rgp120are extracted by preparing cytoplasmic fraction proteins (Fouts et al, supra). In brief, the strains are streaked onto LB-agar containing 8 μ/ml TTAB and grown at 37° C. for 16 hours. Several single colonies from these plate-grown bacterial cultures are transferred to LB-broth containing 8 μg/ml TTAB so that the starting optical density at 600 nm is 0.05 relative to a sterile control. These liquid cultures are incubated at 37° C. with shaking until the optical density at 600 nm becomes 0.8 relative to a sterile control. The bacteria are harvested by centrifugation and resuspended in PBS at a density of $10^{10}$ cfu/ml. These bacterial suspensions are sonicated on ice for 5 minutes in 30 second bursts. The unlysed bacterial cells are removed by centrifugation at 5000×g. The supernatants containing rgp120and the control supernatants are collected and filter-sterilized though a 0.45 μM filter (Millipore). The rgp120and cell membranes are collected by centrifugation at 45,000 g for 30 min. The pellet is resuspended-in Triton X-100 (1% (w/v)) and incubated at 37° C. for 30 min. Then rgp120 is separated from the detergent-solubilized membranes by centrifugation at 45,000×g for 30 min (Fouts et al, supra). The pellet containing rgp120 is collected and filter-sterilized through a 0.45 μM filter (Millipore) and dialysed against 10,000 volumes of PBS at 4° C. (Fouts et al, supra). The level of rgp120 present in these preparations is evaluated by capture ELISA and examined by immunoblot (Fouts et al, supra).

To meausure the immunogenicity of the said rgp120, the crude preparations of rgp120 are mixed with FIA at a final concentration of 1 mg/ml as described (Harlow and Lane (eds), supra pp53–137). Then groups of 5 C57BL/6 mice aged 4–6 weeks are immunized with 100 μg of non-pyrogenic and pyrogenic rgp120 each, subcutaneously (Harlow and Land (eds), supra pp53–137). The mice are given a booster immunization containing the same dose 30 days after the primary immunization. Serum is collected before and on days 14, 28, 44 and 60 after immunization. About 400–500 μl of blood is collected into individual microfuge tubes from the tail vein of each mouse and allowed to clot by incubating for 16 hrs at 4° C. After centrifugation in a microfuge for 5 min, the sera samples are transferred to fresh tubes and stored at −20° C. Serum IgG against rgp120 is measured by ELISA (Coligan et al (eds), supra pp2.1.1–2.1.22; Harlow and Lane (eds), supra pp553–614).

To assay the endotoxin activity of MLK53(pTRF2) supernatants versus the W3110(pTRF2) rgp120, aliquots of each rgp120 (ranging from 1 ng to 10 μg) in 10-fold serial dilutions from strain MLK53(pTRF2) and W3110(pTRF2) are added to triplicate wells of a 96 well microtiter plate. Then, 5×$10^5$ PBMCs are added to these wells control wells contained only PBMCs (negative control) or PBMCs with 10 ng/ml purified *E. coli* LPS (Sigma, St Louis Mo.) (positive control). Culture supernatants are collected after 8 hours incubation at 37° C. in 5% $CO_2$ and TNFα levels are measured by TNFα-specific quantitative ELISA (Pharminogen).

The results show that non-pyrogenic host strain MLK53 is a useful host for the production of non-pyrogenic and immunogenic rgp120.

EXAMPLE 8

Non-pyrogenic Inactive Bacterial Vaccines

Parenteral whole cell killed vaccines should display acceptable safety and immunogenicity properties (Crytz (ed), supra; Woodrow and Levine (eds), supra). To measure the safety of *E. coli* htr B as a parenteral whole cell killed vaccine, galactosamine-sensitized C57BL/6 mice are injected with doses of these baccilli suspended in saline. First, non-pyrogenic strain MLK53 is grown in LB agar and LB broth at 37° C. as outlined above in example 1. The bacteria are harvested by centrifugation at 5000×g and washed 2 times with normal saline. After the final centrifugation, the bacteria are resuspended in normal saline to a concentration of 5×$10^{10}$ cfu/ml. Groups of 7 C57BL/6 mice are galactosamine-sensitized by injecting each mouse with galactosamine (Sigma; 300 mg/kg) intravenously (Galanos et al, supra). On the same day the mice are immunized intraperitonelally with 10-fold serial doses from $10^3$ to $10^{10}$ cfu of the *E. coli* htr B. The dose of bacteria that causes 50% death of the mice ($LD_{50}$ values) is calculated by interpolation after 72 hours as described (Welkos and O'Brien, supra). Wild type *E. coli* is used as virulent control. This murine safety assay demonstrates the safety of the *E. coli* non-pyrogenic whole cell killed bacterial vaccine.

To measure the immunogenicity of *E. coli* btr B as a parenteral whole cell killed vaccine, normal mice are injected with doses of these baccilli suspended in saline. First, non-pyrogenic strain MIK53 is grown in LB agar and LB broth at 37° C. as outlined above in example 1. The bacteria are harvested by centrifugation at 5000×g and washed 2 times with normal saline. After the final centrifugation, the bacteria are resuspended in normal saline to a concentration of 5×$10^{10}$ cfu/ml. Then, groups of C57BL/6 mice aged 4–6 weeks are immunized subcutaneously with $10^8$, $10^9$, or $10^{10}$ cfu each of the non-pyrogenic *E. coli* htr B (Harlow and Land (eds), supra pp53–137). On day 30 after the primary immunization, the mice are boosted with the identical doses. Serum is collected before and on days 28 and 44 after immunization. Serum IgG and IgA against *E. coli* LPS will be measured by ELISA (Coligan et al (eds), supra pp2.1.1–2.1.22; Harlow and Lane (eds), supra pp553–614). This mouse immunogenicity assay shows that the whole cell killed non-pyrogenic bacterial vaccine is immunogenic.

EXAMPLE 9

Analysis of Live Bacterial Vaccine Potential

A live bacterial vaccine must be safely attenuated so that is does not induce adverse clinical reactions and immunogenic so that it elicits protective immunity (Woodrow and Levine (eds), supra). The balance between hypo-attenuation, effective-attenuation and hyper-attenuation is a fine line. Hypo-attenuation herein refers to the degree of attenuation in a bacterial vaccine strain that results in some level of residual virulence in the host. Effective-attenuation herein refers to the a level of attenuation that results in a bacterial vaccine strain being well tolerated and immunogenic. Hyper-attenuation herein refers to the level of attenuation that results in a bacterial vaccine strain being well tolerated but poorly immunogenic. One cannot predict how a particular mutant class will behave with respect to these groupings without first conducting safety and immunogenicity experiments in a relevant animal model.

The utility of the htrB mutation as an attenuating lesion is addressed using the hog gastric mucin virulence assay (Hone et al, supra), the mouse-typhoid model (Mackaness et al, *J Exp Med* 124:573–584 (1966); Blanden et al, *J Exp Med* 124:585–600 (1966); and Collins et al, *J Exp Med* 124:601–612 (1966)), and the Shigella guinea pig virulence and immunogenicity assays (Sereny, *Acta Microbial Acad Sci Hung* 4:367–376 (1957); and Noriega et al, *Infect Immun* 62:5158–5172 (1994)).

To assay the virulence of the *E. coli* htrB vaccine strain MLK53, the bacteria are grown at 37° C. for 16 hours on L-agar with TTAB (8 µg/ml). Wild type *E. coli* W3110 is used as virulent control and grown under the identicle conditions. These overnight cultures are subcultured into LB broth with TTAB (8 µ/ml) at a starting optical density of 0.05 relative to a sterile LB broth control and grown at 37° C. with shaking to an optical density (600 nm) of 0.8 relative to a sterile LB broth control. The bacteria are harvested by centrifugation at 5000×g, washed in PBS and suspended in 10-fold serial dilutions in 5% Hog Gastric Mucin as described (Hone et al, supra). Briefly, equal volumes of 10-fold serial dilutions of the bacterial suspensions are mixed with 10.0% (w/v) hog gastric mucin (Wilson Laboratories). The bacterial dilutions suspended in 5.0% (w/v) hog gastric mucin were injected intraperitoneally into 18–20 g female CD-1 mice (Charles River, Pa.). The dose of bacteria that causes 50% death of the mice ($LD_{50}$ values) is calculated by interpolation after 72 hours as described (Hone et al, supra). Wild type *E. coli* strain W3110 (Karow and Georgopoulos, supra) is used as virulent control. This procedure revealed the $LD_{50}$ of wild type *E. coli* W3110 is $4.9 \times 10^5$ and the LD50 of *E. coli* htr mutant MLK53 is $>4.2 \times 10^8$. Thus, the htrB mutation resulted in greater than 850-fold attenuation.

The mouse-typhoid model (Mackaness et al, supra; Blanden et al, supra; and Collins et al, supra) can also be used to address issues surrounding the development of bacterial htrB mutants as vaccines and vaccine vectors.

First, a Salmonella htrB mutant is constructed. To accomplish this, the htrB::Tn10 allele is moved into virulent *S. typhimurium* and attenuated *S. typhimurium* ΔaroA strains using standard bacteriophage-mediated transduction techniques as described (Miller (ed), supra). That is htrB::Tn10 is transduced into wild type *S. typhimurium* SL1344 and Δaro strain SL3261 (Hoiseth and Stocker, supra), resulting in a single mutant SL1344 htrB::Tn10, and a double mutant SL3261 Δaro, htrB::Tn10, respectively.

Salmonella strains SL1344, SL3261 Δaro, SL3261 Δaro, htrB::Tn10 and SL1344 htrB::Tn10 are cultured on LB agar and LB broth at 37° C. as described above in example 1. The bacteria are harvested by centrifugation at 5000×g, washed in PBS and after the final centrifugation step are suspended in PBS at a concentration of $5 \times 10^{10}$ cfu/ml. Then groups of 10 female C57BL/6 mice aged 4–6 weeks are given 0.2 ml of a 50% saturated solution of sodium bicarbonate by gastric intubation to neutralize gastric acidity (Hone et al, supra). Then 5 minutes after the bicarbonate these groups of 10 mice are immunized orally with 0.1 ml (ie. $10^9$ cfu) of these suspensions (ie. SL1344, SL3261 Δaro, SL3261 Δaro, htrB::Tn10 and SL1344 htrB::Tn10 by gastric intubation (Hone et al, *Microbial Path* 5:407–418 (1987)). Serum is collected at days 0, 15, 30, and 45 after immunization. Finally, serum IgM, IgG and IgA responses induced by each strains is determined by ELISA using whole Salmonella as antigen (Coligan et al (eds), supra pp2.1.1–2.1.22; Harlow and Lane (eds), supra pp553–614). The results of this experiment show that SL3261 Δaro, SL3261 Δaro, htrB::Tn10 and SL1344 htrB::Tn10 are attenuated and immunogenic. The control mice that receive wild type *S. typhimurium* SL1344 are killed by this lethal dose within two weeks.

Alternatively, the htrB::Tn10 mutant allele can be introduced into Shigella flexneri and the vaccinal properties of such a non-pyrogenic Shigella vaccines can be evaluated in guinea pigs (Sereny, supra; and Noriega et al, supra).

First, the htrB::Tn10 allele is introduced into *Shigella flexneri* 2a strain 2457T (Formal et al, *J Infect Dis* 164:533–537 (1991)) by a standard well known P1-mediated transduction procedure (Miller (ed), supra). In brief, bacteriophage P1vir lysates are made from strain MLK53 as described (Miller (ed), supra). Then strain 2457T is treated with these lysates and tetracycline-resistant transductants are selected as described (Miller (ed), supra). These mutants are checked for the expression of O-polysaccharide by slide agglutination as described (Noriega et al, supra). Also, the ability of 2457T htrB::Tn10 to invade is verified by the well-known Shigella invasion assay (Noiega et al, supra). A strain that is invasive and expresses O-polysaccharide is selected for further evaluation.

The guinea pig keratoconjunctovitis assay is the classical test of Shigella virulence (Sereny, supra and Noriega et al, supra). A dose response to wild type 2457T and non-pyrogenic strain 2457T htrB::Tn10 is conducted as described (Noriega et al, supra). In brief, Shigella strains 2457T and 2457T htrB::Tn10 are grown on LB agar and LB broth at 37° C. as described above in example 1. The bacteria are harvested by centrifugation at 5000×g, washed in PBS and after the final centrifugation step are suspended in endotoxin-free PBS at a concentration of $2 \times 10^{10}$ cfu/ml. About 50 µl of these suspensions is administered to the conjuctiva of groups of 20 female guinea pigs aged 6 to 8 weeks (Charles River). The eyes are monitored for a period of one week for the development of conjunctavitis (Sereny, supra). This experiment shows that non-pyrogenic strain 2457T htrB::Tn10 is attenuated compared to wild type parent 2457T.

Guinea pigs are also used to evaluate to vaccinal properties of non-pyrogenic strain 2457T htrB::Tn10 as described (Noriega et al, supra). In brief, Shigella strain 2457T htrB::Tn10 and negative control strain MLK53 are grown on LB agar and LB broth at 37° C. as described above in example 1. The bacteria are harvested by centrifugation at 5000×g, washed in PBS and after the final centrifugation step are suspended in endotoxin-free PBS at a concentration of $2 \times 10^{10}$ cfu/ml. Then groups of 15 female guinea pigs aged 6–8 weeks are given 0.4 ml of a 50% saturated solution of sodium bicarbonate by gastric intubation to neutralize gastric acidity (Noriega et al, supra). About 5 minutes later these guinea pigs a immunized orally with 200 µl of the said Shigella 2457T htrB::Tn10 and *E. coli* MLK53 suspensions by orgiastic intubation (Noriega et al, supra). A second identicle immunization is given 15 days later. Tears are collected from each guinea pig before and on days 7, 14 and 21 after vaccination (Noriega et al, supra). These tear samples are used to quantitate Shigella-specific IgA response that manifest after immunization by ELISA as described (Noriega et al, supra; Coligan et al (eds), supra pp2.1.1–2.1.22; Harlow and Lane (eds), supra pp553–614). This experiment shows that attenuated Shigella strain 2457T htrB::Tn10 is immunogenic. Collectively, the virulence and immunogenicity experiments with non-pyrogenic strain 2457T htrB::Tn10 show that this strain is a candidate 2457T htrB::Tn10 vaccine and vaccine vector for use in humans.

EXAMPLE 10

Development of Non-pyrogenic Bacterial Vaccine Vectors

Infection with ETEC ranks high as a public health problem in developing countries and to travelers from developed countries who visit ETEC-endemic regions (Levine, *Scand J Gastroenterol* 18:121–143 (1983); Levine, *J Infect Dis* 155:377–389 (1987)). Currently, there is a need to develop a safe and effective ETEC vaccine to serve as a public health tool for the prevention of ETEC infection (Levine, supra (1983); Levine, supra (1987); Kaper and Levine, *Vaccine* 6:197–200 (1988); Tacket et al, *Vaccine* 12:1270–1274 (1994); and Yamamoto et al, *Infect Immun* 50:925–928 (1985)). Purified ETEC colonization factor antigens (CFAs), which mediate attachment to enterocytes in the small intestine (Evans et al, *Infect Immun* 12:656–667 (1975); Evans et al, *Infect Immun* 18:330–337 (1977)) stimulated protective antibodies in animal models (de la Cabada et al, *J Exp Med* 11:303–308 (1981)). Volunteers who ingested a purified preparation of an ETEC fimbriae, however, did not mount an effective mucosal immune response (Lark et al (eds), In: *Protein-carbohydrate interactions in biological systems: The molecular biology of microbial pathogenicity*. Academic Press, London England. pp143–152 (1986)), probably due to denaturation and degredation of the antigen by gastric acidity and proteases (Schmidt et al, *Gastroenterol* 82:1575–1582 (1985)). Effective immunization of volunteers with purified ETEC fimbriae was achieved, though, when this antigen was delivered directly to the intestine by orgiastic intubation (Lark et al, supra). This clinical study demonstrated the need for a means to effectively deliver ETEC CFAs to the mucosal immune system of the intestine.

One solution is to express CFA in a live oral vaccine vector (Yamamoto et al, supra). Studies with Salmonella expressing porcine ETEC fimbriae K88 demonstrate that such vaccine vectors elicit mucosal and serum antibody against the fimbrial antigen (Hone et al, supra (1988); Stevenson and Manning, *FEMS Lett* 28:317–320 (1985)).

To evalate the effectivenes of non-pyrogenic strains as vaccine vectors plasmid pJGX15C is introduced S. *typhimurium* ΔaroA strain SL3261 (Hoiseth and Stocker, supra) and S. *typhimurium* SL1344 ΔhtrB mutant strains (from example 9) by standard transformation procedures (Sambrook et al (eds), supra). Plasmid pJGX15C expresses CFA/I (Wu et al, *Infect Immun* 63:In press (1995)) when these strains are grown on LB agar and LB broth (Difco) supplemented with TTAB (8 μg/ml) as described in example 1 above. CFA/I expression is confirmed by colony immunoblots (Sambrook et al, supra). Comparative immunoblot analysis of SDS-polyacrylamide gel electrophoresis (SDS-PAGE)-separated CFA/I preparations from SL3261(pJGX15C) and S. typhimuirum ΔhtrB(pJGX15C) is performed as described (Hall et al, *J Bacteriol* 171:6372–6374 (1989)). In brief, the bacterial strains are incubated at 37° C. for 16 hr on LB agar supplemeted with TTAB (8 μg/ml). Wild type ETEC strain H10407 (Evans et al, supra (1977)) was used as a CFA/I positive control. Bacteria are harvested by wiping these plates with a sterile cotton wool swab and suspended in PBS. The optical densities of these suspensions are adjusted so that there are $10^8$ cfu/ml. Then, 1 ml of each adjusted suspensions is placed into a microfuge tube and centrifuged at 12,000×g for 5 min. The bacterial pellets are resuspended in 40 μl of 1×SDS-PAGE loading buffer and boiled for 5 min (Hall et al, supra). After boiling bacterial cells are removed by centrifugation and 20 μl samples of the cell-free supernatants, containing solubilized CFA/I pilin subunits, are loaded onto a 15% (w/v) SDS-polyacrylamide gel and electrophoresed at 80 mV for 2 hr. After electrophoresis the proteins are transferred (10 mV for 16 hr) from the SDS-polyacrylamide gel to 0.2 μM nitrocellulose membranes (BioRad) as described (Sambrook et al (eds), supra).

These membranes are probed first with primary antibody (HB101-absorbed rabbit polyclonal anti-CFA/I serum raised using purified CFA/I from H10407 (Hall et al, supra), then with secondary antibody (goat anti-rabbit IgG conjugated to horseradish peroxidase (Amersham, Arlington Heights, Ill.)). Detection of primary antibody-reactive protein bands is achieved by chemilumwnescence (Amersham).

To assess the immunogenicity of the Salmonella-CFA/I recombinants, Salmonella strains SL3261(pJGX15C) and SL1344 htrB::Tn10 (pJGX15C) and control strains SL3261 and SL1344 htrB::Tn10 are cultured in LB agar and LB broth at 37° C. as described above in example 1. The bacteria are harvested by centrifugation at 5000×g, washed in PBS and after the final centrifugation step are suspended in PBS at a concentration of $5 \times 10^{10}$ cfu/ml. Then groups of 10 female C57BL/6 mice aged 4–6 weeks are given 0.2 ml of a 50% saturated solution of sodium bicarbonate by gastric intubation to neutralize gastric acidity (Hone et al, supra). Approximately 5 minutes after the bicarbonate these groups of 10 mice are immunized orally with 0.1 ml (ie. $10^9$ cfu) of these suspensions (ie. SL3261(pJGX15C) and SL1344 htrB::Tn10 (pJGX15C) and control strains SL3261 and SL1344 htrB::Tn10) by gastric intubation (Hone et al, *Microbial Path* 5:407–418 (1987)). Serum is collected at days 0, 15, 30, and 45 after immunization.

Serum IgG responses to CFA/I in these sera samples are quantitated by ELISA (Tacket et al, supra). Purified CFA/I fimbrial antigen was prepared as described (Hall et al, supra) and suspended in PBS (pH 7.2) at a concentration of 1 μg/ml and used to coat 96-well ELISA plates (Maxisorp, Nunc). Goat anti-mouse IgG conjugated to horseradish peroxidase (1 μg/ml; Southern Biotechnology Associates, Birmingham, Ala.) was used to detect CFA/I-specific serum IgG. Endpoint titers were calculated by taking the inverse of the last serum dilution giving an absorbance ≧0.1 OD units above the $OD_{405}$ of negative controls after 30 min incubation (Tacket et al, supra).

The ELISA results show that non-pyrogenic bacteria are effective vaccine vectors for the delivery of foreign antigens.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

We claim:

1. A method for preparing a culture comprising a non-pyrogenic bacterial vaccine, said method comprising the steps of:

(a) genetically modifying a gram-negative host bacterial strain that is suitable for use as a vaccine, said step of genetically modifying comprising introducing a conditional mutation in one or more genes selected from the group consisting of kdsA, kdsB, kdtA, lpxA, lpxB, lpxC, lpxD, ssc, pmr, htrB and msbB of the gram-negative host strain, wherein the conditional mutation affects the biosynthesis of lipid A under non-permissive culture conditions, and results in the synthesis of non-pyrogenic lipid A; and (b) culturing the genetically modified gram-negative host strain in non-permissive culture conditions to produce non-pyrogenic lipid A thereby generating a non-pyrogenic vaccine.

2. The method according to claim 1 wherein said non-permissive culture conditions include a quaternary cationic compound selected from the group consisting of: tetraacyltetraethylammonium bromide, polylysine, polymyxin, ethanolamine dimethyldictadecylammonium bromide, 1,2, diacyl-3-trimethylammoniumpropane, 2-dioleyloxy-N-[2 (perminecarboxamindo)-ethyl]-N,N-dimethyl-1-propanammoniumtrifluoroacetate, [1-(2,3-diol-eyloxy) propyl]-N,N,N-trimethylammonium chloride.

3. The method according to claim 1, wherein said mutation further results in the accumulation of lipid A precursors.

4. A method for producing a non-pyrogenic bacterial strain, said method comprising the steps of:

(a) genetically modifying a gram negative bacterial strain, said step of genetically modifying comprising introducing into the genome of the gram negative bacterial strain a conditional mutation which affects the biosynthesis of lipid A under non-permissive culture conditions, and results in the synthesis of non-pyrogenic lipid A;

(b) culturing the genetically modified gram negative bacterial strain of (a) in a medium under non-permissive culture conditions, wherein the medium comprises a modified gram-negative bacterial strain producing non-pyrogenic lipid A; and (c) isolating the modified gram negative bacterial strain producing non-pyrogenic lipid A from the medium.

5. The method according to claim 4, wherein said mutation comprises a mutation of a gene selected from the group consisting of htrB, msbB, kdsA, kdsB, and kdtA.

6. The method according to claim 4, wherein said mutation results in the accumulation of lipid A precursors.

7. The method of claim 6, wherein said culturing step is carried out at a temperature from about 35° C. to about 44° C.

8. The method according claim 5, wherein said mutation comprises a mutation of a gene selected from the group consisting of htrB and msbB.

9. A method for preparing a culture comprising a non-pyrogenic bacterial strain, said method comprising the steps of:

(a) genetically modifying a gram-negative host bacterial strain that is suitable for use as a vaccine, said step of genetically modifying comprising introducing a conditional mutation in one or more genes selected from the group consisting of kdsA, kdsB, kdtA, lpxA, lpxB, lpxC, lpxD, ssc, pmr, htrB and msbB of the gram-negative host strain, wherein the conditional mutation affects the biosynthesis of lipid A under non-permissive culturing conditions, and results in the synthesis of non-pyrogenic lipid A; and (b) culturing the genetically modified gram-negative host strain in non-permissive culture conditions to produce non-pyrogenic lipid A thereby generating a non-pyrogenic vaccine, wherein the non-permissive culture conditions include temperature of 35° C. to 44° C. and quaternary cationic compound presence.

* * * * *

UNITED STATES PATENT AND TRADEMARK OFFICE
CERTIFICATE OF CORRECTION

PATENT NO. : 6,548,287 B1  
DATED : April 15, 2003  
INVENTOR(S) : Powell et al.

Page 1 of 3

It is certified that error appears in the above-identified patent and that said Letters Patent is hereby corrected as shown below:

Title page,
Item [62], Related U.S. Application Data, change "Feb. 19, 1997" to -- Nov. 21, 1996 --.

Column 1,
Line 8, change "Feb. 19, 1997" to -- Nov. 21, 1996 --.
Line 22, change "tile" to -- the --.

Column 2,
Line 23, change "5(111" to -- 5(11) --.
Line 48, change "he" to -- be --.

Column 4,
Line 52, change "i992" to -- 1992 --.

Column 6,
Line 39, change "TNF-60" to -- TNF-α --.
Line 50, after "supra)" insert -- . --.

Column 10,
Line 29, change "290" to -- 2490 --.
Line 41, change "paq" to -- pag --.
Line 42, change "1939" to -- 1989 --.
Line 43, change "picA" to -- plcA --.
Line 60, change "phiA" to -- phlA --.

Column 12,
Line 48, change "schuberil" to -- schuberii --.
Line 56, change "car" to -- can --.
Line 65, change "pneumonia" to -- pneumoniae --.

Column 13,
Line 2, change "influenza" to -- influenzae --.

Column 15,
Line 55, change "62:69-79" to -- 622:69-79 --.

Column 17,
Line 31, "48:351-358" to -- 43:351-358 --.

Column 18,
Line 4, change "α-chain" to -- β-chain --.
Line 53, change "1933" to -- 1993 --.

UNITED STATES PATENT AND TRADEMARK OFFICE
CERTIFICATE OF CORRECTION

PATENT NO. : 6,548,287 B1
DATED : April 15, 2003
INVENTOR(S) : Powell et al.

It is certified that error appears in the above-identified patent and that said Letters Patent is hereby corrected as shown below:

Column 19,
Line 19, change "Vixol" to -- Virol --.

Column 20,
Line 41, change "Zn" to -- In --.
Line 53, change "abdications," to -- Applications --.

Column 22,
Line 55, change "pro," to -- prg --.
Line 57, change "picA" to -- plcA --.

Column 23,
Line 5, change "17o" to -- 170 --.
Line 7, change "phiA" to -- phlA --.
Line 56, change "Adeauate" to -- Adequate --.

Column 26,
Line 1, change "Adecuate" to -- Adequate --.

Column 27,
Line 6, change "DH5A" to -- DH5α --.
Line 31, change "TNFA" to -- TNFα --.
Line 38, change "DHSα" to -- DH5α --.
Lines 43-44, change "macrophaae: the natural immune system" to -- Macrophage: The Natural Immune System --.

Column 28,
Line 49, change "htxB" to -- htrB --.

Column 30,
Line 64, change "8 $\mu$/ml" to -- 8 $\mu$g/ml --.

Column 31,
Line 31, change "$\mu$m" to -- gm --.

Column 32,
Line 34, change "*coil*" to -- *coli* --.

Column 33,
Line 13, change "(1q95)" to -- (1995) --.
Line 20, change "$\mu$/ml" to -- $\mu$g/ml --.

UNITED STATES PATENT AND TRADEMARK OFFICE
CERTIFICATE OF CORRECTION

PATENT NO. : 6,548,287 B1
DATED : April 15, 2003
INVENTOR(S) : Powell et al.

It is certified that error appears in the above-identified patent and that said Letters Patent is hereby corrected as shown below:

Column 34,
Line 1, change "wells control" to -- wells. Control --.
Line 37, change "btr" to -- htr --.
Line 40, change "MIK53" to -- MLK53 --.

Column 35,
Line 25, change "8 $\mu$/ml" to -- 8 $\mu$g/ml --.

Column 36,
Line 65, change "orgiastic" to -- orogastric --.

Column 37,
Line 42, change "orgiastic" to -- orogastric --.

Column 38,
Line 23, change "chemilumwnesecne" to -- chemiluminescence --.

Signed and Sealed this

Sixteenth Day of December, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,548,287 B1
DATED         : April 15, 2003
INVENTOR(S)   : Powell et al.

It is certified that error appears in the above-identified patent and that said Letters Patent is hereby corrected as shown below:

Column 1,
Line 11, insert -- The development of this invention was supported by the University of Maryland, Baltimore, Maryland and NIH funding, NIH-5-ROI-A132879 --.

Signed and Sealed this

Thirteenth Day of June, 2006

JON W. DUDAS
*Director of the United States Patent and Trademark Office*